(12) United States Patent
Tamai et al.

(10) Patent No.: US 8,460,288 B2
(45) Date of Patent: Jun. 11, 2013

(54) BIOLOGICAL-TISSUE JOINING APPARATUS

(75) Inventors: Masato Tamai, Tokyo (JP); Akihiro Horii, Tokyo (JP); Hiroshi Kakidachi, Tokyo (JP); Masaki Hayashi, Tokyo (JP); Aki Okubo, Tokyo (JP); Hiroshi Takahashi, Tokyo (JP)

(73) Assignee: Olympus Corporation, Tokyo (JP)

( * ) Notice: Subject to any disclaimer, the term of this patent is extended or adjusted under 35 U.S.C. 154(b) by 739 days.

(21) Appl. No.: 12/638,013

(22) Filed: Dec. 15, 2009

(65) Prior Publication Data

US 2011/0098700 A1    Apr. 28, 2011

(30) Foreign Application Priority Data

Oct. 28, 2009  (JP) ................................. 2009-248163
Nov. 11, 2009  (JP) ................................. 2009-258169

(51) Int. Cl.
*A61B 18/18*    (2006.01)
(52) U.S. Cl.
USPC ................................. 606/41; 606/213; 606/27
(58) Field of Classification Search
USPC ................ 606/27, 51, 52, 205, 207, 213–316
See application file for complete search history.

(56) References Cited

U.S. PATENT DOCUMENTS

| | | | |
|---|---|---|---|
| 6,605,066 B1 | 8/2003 | Gravagna et al. | |
| 6,730,299 B1 | 5/2004 | Tayot et al. | |
| 7,571,845 B2* | 8/2009 | Viola | 227/180.1 |
| 8,157,830 B2* | 4/2012 | Wenchell | 606/186 |
| 2002/0165541 A1* | 11/2002 | Whitman | 606/48 |
| 2003/0171748 A1 | 9/2003 | Truckai et al. | |
| 2006/0085031 A1* | 4/2006 | Bettuchi | 606/215 |
| 2008/0283577 A1* | 11/2008 | Boyden et al. | 227/181.1 |
| 2010/0076429 A1* | 3/2010 | Heinrich | 606/49 |

FOREIGN PATENT DOCUMENTS

| | | |
|---|---|---|
| EP | 0 341 007 A2 | 4/1989 |
| JP | 2-71747 A | 3/1990 |
| JP | 6-327684 A | 11/1994 |
| JP | 7-23970 A | 1/1995 |
| JP | 9-225019 A | 9/1997 |
| JP | 11-104143 | 4/1999 |
| JP | 2000-290633 A | 10/2000 |
| JP | 2001-054523 | 2/2001 |
| JP | 2002-526192 A | 8/2002 |
| JP | 2003-504159 A | 2/2003 |
| JP | 2003-235977 | 8/2003 |
| JP | 2005-515808 A | 6/2005 |
| JP | 2006-501938 A | 1/2006 |
| JP | 2006-55637 A | 3/2006 |

(Continued)

*Primary Examiner* — Linda Dvorak
*Assistant Examiner* — Jocelyn D Ram
(74) *Attorney, Agent, or Firm* — Scully, Scott, Murphy & Presser, P.C.

(57) ABSTRACT

Regardless of the type of biological tissue, a sufficient joining force can be quickly obtained; the problem of an adhesive bonding biological tissue other than the target biological tissue can be prevented; and the adhesive can be prevented from becoming impossible to apply due to curing. There is provided a biological-tissue joining apparatus including an energy supplying part that clamps, with pressure, biological tissue to be joined and melts protein in the clamped biological tissue by supplying energy to the biological tissue; and an adhesive supplying part that supplies an adhesive to the biological tissue, wherein the adhesive supplying part includes a discharge port that discharges the adhesive to a contact surface of the energy supplying part in contact with the biological tissue.

9 Claims, 23 Drawing Sheets

FOREIGN PATENT DOCUMENTS

| | | | |
|---|---|---|---|
| JP | 2006-110357 | | 4/2006 |
| JP | 2008-301955 | * | 12/2008 |
| WO | WO 2004/032776 | A1 | 4/2004 |
| WO | WO 2006/044494 | A2 | 4/2006 |

* cited by examiner

BIOLOGICAL-TISSUE JOINING APPARATUS

BACKGROUND OF THE INVENTION

1. Field of the Invention

The present invention relates to a biological-tissue joining apparatus.

This application is based on Japanese Patent Applications Nos. 2007-150684, 2009-248163, and 2009-258169 the content of which is incorporated herein by reference.

2. Description of Related Art

Conventionally, there is a known joining apparatus that joins biological tissue by clamping a stacked pair of pieces of biological tissue and applying ultrasonic energy (for example, refer to Japanese Unexamined Patent Application, Publication No. HEI-11-104143). Moreover, there is a known ultrasonic incising apparatus that is capable of carrying out clotting, cutting, and hemostasis of biological tissue for surgery, such as abdominal surgery or endoscopic surgery, at a temperature lower than an electrosurgical knife and capable of simultaneously carrying out hemostasis and incising (for example, refer to Japanese Unexamined Patent Application, Publication No. 2001-54523).

Moreover, there is a known apparatus that administers biological material, such as a biological adhesive, for carrying out surgical procedures, such as hemostasis, joining and sealing of tissue, during abdominal surgery or endoscopic surgery (for example, refer to Japanese Unexamined Patent Application, Publication Nos. 2003-235977 and 2006-110357).

Although, biological tissue can be joined with the joining apparatus in Japanese Unexamined Patent Application, Publication No. HEI-11-104143 by merely clamping and supplying ultrasonic energy to the biological tissue, in some cases, it may be difficult to maintain a stable joined state of the joined biological tissue because a sufficient joining force is not obtained due to individual differences of the biological tissue, or the flexibility may decrease because of hardening of the biological tissue after joining.

With the apparatus in Japanese Unexamined Patent Application, Publication No. 2001-54523, the sites that can be cut may be limited to small sites with a small vascular diameter since efficient hemostasis cannot be carried out because temperature rises only locally with clotting by ultrasound.

Furthermore, such as in Japanese Unexamined Patent Applications, Publication Nos. 2003-235977 and 2006-110357, immediate treatment may not be carried out because curing of the adhesive in the joining area takes time when a biological adhesive is merely applied.

When the operation of bonding a joining site is carried out repeatedly by applying an adhesive, in some cases, the adhesive gradually cures inside a supply channel, and thus a sufficient amount of adhesive cannot be applied.

When a joining site is bonded by applying an adhesive, in some cases, tissue other than the target tissue may be bonded because the adhesive spatters, is applied excessively, and/or remains uncured when the adhesive is a two-component mixing type.

BRIEF SUMMARY OF THE INVENTION

It is an object of the present invention to provide a biological-tissue treating apparatus that, regardless of the type of biological tissue, is capable of immediately obtaining a sufficient joining force, preventing a problem of an adhesive bonding biological tissue other than the target biological tissue, and preventing the inability to apply the adhesive due to curing.

A biological-tissue joining apparatus according to an aspect of the present invention includes an energy supplying part that clamps, with pressure, biological tissue to be joined and melts protein in the clamped biological tissue by supplying energy to the biological tissue; and an adhesive supplying part that supplies an adhesive to the biological tissue, wherein the adhesive supplying part includes a discharge port that discharges the adhesive to a contact surface of the energy supplying part in contact with the biological tissue.

With the biological-tissue joining apparatus according to an aspect of the present invention, by supplying energy with an energy-supplying part in a state in which biological tissue to be joined is clamped with pressure, protein in the biological tissue melts and seeps into the gap between the biological tissue pieces to be joined and, by using this as an adhesive, enables bonding and joining of the biological tissue. In such a case, when the amount of collagen contained in the biological tissue is small, the shortfall in the amount of collagen can be supplied by operating the adhesive supplying part and discharging collagen, which is used as an adhesive, from the discharge port formed in the contact surface with the biological tissue, and thus a stable joined state can be established.

In the above-described aspect, the adhesive may be collagen, and the adhesive supplying part may include a collagen-supply control part that adjusts the supply rate of the collagen.

In this way, the supply rate of the collagen is adjusted by the operation of the collagen-supply control part; therefore, even when the collagen content differs depending on the type of the biological tissue to be joined, a satisfactory amount of collagen can be supplied, and thus a stable joined state can be established.

In the above-described aspect, an elastin supplying part that supplies elastin to the biological tissue may be further included, wherein the elastin supplying part may include a discharge port that discharges the elastin to the contact surface of the energy supplying part in contact with the biological tissue.

In this way, elastin is discharged from the discharge port formed in the contact surface with the biological tissue by the operation of the elastin supplying part; therefore, hardening of the biological tissue due to elastin seeping out of the biological tissue due to energy supply can be suppressed, and the elasticity of the biological tissue can be maintained.

In the above-described aspect, the elastin supplying part may include an elastin-supply control part that adjusts the supply rate of the elastin.

In this way, the supply rate of the elastin is adjusted by the operation of the elastin-supply control part; therefore, even when the elastin content differs depending on the type of the biological tissue to be joined, a satisfactory amount of elastin can be supplied, and thus the elasticity of the biological tissue can be maintained.

In the above-described aspect, the energy supplying part may be disposed such that it clamps the biological tissue to be joined and may include an electrode that applies electricity to the biological tissue.

In this way, energy can be easily applied to the region to be joined in the biological tissue by applying electricity by clamping the biological tissue to be joined with the electrodes, and collagen is melted for carrying out joining.

In the above-described aspect, the energy supplying part may be disposed such that it clamps the biological tissue to be joined and may include an ultrasonic transducer that supplies ultrasonic waves to the biological tissue.

In this way, energy can be easily applied to the region to be joined in the biological tissue by applying ultrasonic vibration by clamping the biological tissue to be joined with the ultrasonic transducer, and collagen is melted for carrying out joining.

A biological-tissue treating apparatus according to an embodiment of the present invention includes a gripper that clamps biological tissue to be joined; and an adhesive supplying part that supplies an adhesive to the biological tissue gripped by the gripper, wherein the adhesive supplying part includes a discharge port that discharges the adhesive to a contact surface of the gripper in contact with the biological tissue and a leakage preventing part that prevents leakage of the adhesive having an adhesion force from a gap between the surface of the biological tissue and the contact surface when the adhesive is discharged from the discharge port.

With the biological-tissue joining apparatus according to an aspect of the present invention, in a state in which the biological tissue to be joined is clamped by the gripper, the clamped biological tissue can be bonded and joined by supplying the adhesives by the adhesive supplying part.

In this way, the adhesive discharged from the discharge port is prevented from leaking from the gap between the biological tissue surface and the contact surfaces by the leakage preventing parts, thus preventing the bonding of other tissue at sites other than the target site.

In the above-described aspect, the gripper may be an energy supplying part that clamps, with pressure, the biological tissue to be joined and may supply energy to the clamped biological tissue to melt collagen inside the biological tissue.

In this way, by supplying energy with an energy supplying part in a state in which biological tissue to be joined is clamped with pressure, collagen in the biological tissue melts and seeps into the gap between the biological tissue pieces to be joined and, by using this as an adhesive, enables bonding and joining of the biological tissue. In such a case, when the amount of collagen contained in the biological tissue is small, the adhesive force of only the collagen seeping out of the biological tissue can be supplemented by operating the adhesive supplying part to discharge the adhesive from the discharge port formed in the contact surface with the biological tissue, and thus a stable joined state can be established.

In the above-described aspect, the leakage preventing part may include a peripheral-wall member surrounding the periphery of the contact surface and may block the adhesive that leaks from the gap between the contact surface and the surface of the biological tissue.

In this way, the adhesive discharged from the discharge port formed in the contact surface surrounded by the peripheral-wall member is blocked by the peripheral-wall member and is prevented from leaking outside.

In the above-described aspect, the peripheral-wall member may be provided in such a manner that the peripheral-wall member protrudes toward the contact surface and may include a driving part that causes the peripheral-wall member to protrude.

In this way, even when the contact surface moves in a direction away from the surface of the biological tissue, the gap in the surroundings of the contact surface can be closed by the peripheral-wall member by driving the driving part so that the peripheral-wall member protrudes, and thus the adhesive can be prevented from leaking outside.

In the above-described aspect, the driving part may be a spring member that biases the peripheral-wall member in a direction protruding from the contact surface.

In this way, when the contact surface closely contacts the surface of the biological tissue, the peripheral-wall member moves in the contact surface direction against the biasing force of the spring member, whereas when the contact surface moves away from the surface of the biological tissue, the peripheral-wall member can be maintained in a close contact state with the surface of the biological tissue by the biasing force of the spring member.

In the above-described aspect, the leakage preventing part may include a suction port, disposed on an outer circumferential position on the contact surface, that sucks the adhesive discharged from the discharge port and a negative-pressure supplying part that evacuates the suction port to negative pressure.

In this way, when the amount of adhesive discharged from the discharge port is excessive, the suction port can be evacuated to negative pressure with the negative-pressure supplying part and the excessive adhesive can be sucked through the suction port in order to prevent leakage of the adhesive to sites other than the target site.

In the above-described aspect, the suction port may be disposed on a side surface adjacent to the contact surface of the energy supplying part.

In this way, the adhesive that is about to leak out from between the contact surface and the surface of the biological tissue can be sucked through the suction port formed in the side surface adjacent to the contact surface in order to prevent leakage from spreading outside.

In the above-described aspect, the leakage preventing part may include a washing-solution discharge port, provided in the proximity of the contact surface, that discharges a washing solution and a washing-solution supplying part that supplies the washing solution to the washing-solution discharge port.

In this way, washing solution can be discharged from the washing-solution discharge port formed in the proximity of the contact surface by operating the washing-solution supplying part in order to wash away the excessive adhesive. As the washing solution, it is preferable to use a solution that has high biological affinity, such as normal saline, lactated Ringer's solution, and phosphate buffered saline. In such a case, the adhesive can be locally diluted, and thus the adhesive force at the surface can be reduced.

In the above-described aspect, the leakage preventing part may include a washing-solution suction port disposed on an outer circumferential position on the contact surface and that sucks the washing solution that is discharged from the washing-solution discharge port and flows along the surface of the adhesive, and a negative-pressure supplying part that evacuates the washing-solution suction port to negative pressure.

In this way, the washing solution that has locally diluted the surface of the adhesive and reduced the adhesive force of the surface can be sucked through the washing-solution suction port by the operation of the negative-pressure supplying part in order to prevent it from spreading through the body.

In the above-described aspect, the adhesive may be an adhesive curable by a physical stimulus, and the leakage preventing part may include a stimulating part that applies the physical stimulus to the adhesive discharged onto the biological tissue.

In this way, curing is promoted by applying a physical stimulus to the adhesive by the operation of the stimulating part, and the adhesive maintaining its adhesive force can be prevented from spreading to sites other than the target side.

In the above-described aspect, the leakage preventing part may include a hardness detector that detects the hardness of the adhesive applied to the biological tissue and an alarm unit that issues an alarm that the hardness detected by the hardness detector is smaller than a predetermined threshold.

In this way, the hardness of the adhesive applied to the biological tissue is detected by the hardness detector, and when it is smaller than the predetermined threshold, an alarm is issued by the alarm unit; therefore, the adhesive can be prevented from being left standing without sufficiently curing. Since an adhesive that is not sufficiently cured may bond tissue other than that in the target site, such a problem can be prevented by removing the biological-tissue treating apparatus after sufficient curing.

A biological-tissue joining apparatus according to an embodiment of the present invention includes an energy supplying part that clamps, with pressure, biological tissue to be joined and melts protein contained in the biological tissue by supplying energy to the clamped biological tissue; and an adhesive supplying part that supplies an adhesive to the biological tissue, wherein the adhesive supplying part includes a supplying member provided with a supply channel that supplies the adhesive to a discharge port opened in a contact surface of the energy supplying part in contact with the biological tissue, wherein the energy supplying part is secured to a main body of the apparatus, and wherein the supplying member is mounted on the main body of the apparatus in a detachable manner.

With the biological-tissue joining apparatus according to an aspect of the present invention, by supplying energy with an energy supplying part in a state in which biological tissue to be joined is clamped, with pressure, by the energy supplying part, protein in the biological tissue melts and seeps into the gap between the biological tissue pieces to be joined and, by using this as an adhesive, enables bonding and joining of the biological tissue. When the amount of protein contained in the biological tissue is small, the adhesive force of only the protein contained in the biological tissue can be supplemented by operating the adhesive supplying part to discharge the adhesive from the discharge port formed in the contact surface with the biological tissue, and thus a stable joined state can be established.

In such a case, the adhesive is supplied to the discharge port through the supply channel provided in the supplying member, and there is a possibility that the adhesive inside the supply channel may cure and cause a clog while the bonding operation of the biological tissue by the energy supplying part and the adhesive supplying part is repeated a plurality of times. In such a case, according to the present invention, a reduction in the discharge rate of the adhesive can be prevented by removing the detachable supplying member from the main body of the apparatus and replacing it, and thus stable bonding can be carried out. Since the energy supplying part is secured to the main body of the apparatus, it can be reused without replacement.

In the above-described aspect, the supplying member may be a flexible tube, and a peristaltic pump that pumps out the adhesive inside the tube while crushing the tube in the radial direction may be provided in the main body of the apparatus.

In this way, the peristaltic pump forming part of the adhesive supplying part can be reused, leaving only the supply member as a consumables, and thus the running cost can be reduced.

In the above-described aspect, the adhesive supplying part may include a flexible adhesive container which is a sealed container enclosing the adhesive, and a needle member that connects the supply channel to the adhesive container by puncturing the adhesive container may be provided at one end of the supply channel formed in the supplying member.

In this way, the replacement cycles of the adhesive container and the supplying member that form part of the adhesive supplying part do not match, and replacement can be carried out separately, preventing residual adhesive. By puncturing the adhesive container with the needle member, the supply channel can be connected to the adhesive container in a sterile manner, and thus dust etc. can be prevented from mixing with the adhesive discharged from the discharge port.

In the above-described aspect, a compressor that compresses the adhesive container may be further included.

In this way, the compression of the adhesive container can be adjusted by the operation of the compressor, and the discharge rate of the adhesive from the discharge port can be adjusted.

In the above-described aspect, the adhesive supplying part may include a syringe having a supply port connected to the supplying member in a detachable manner and may be capable of supplying the adhesive into the supply channel through the supply port.

In this way, the supply rate of the adhesive to the supply channel can be adjusted by the syringe, and the discharge rate of the adhesive from the discharge port can be adjusted.

In the above-described aspect, a pressure part that applies pressure to the syringe may be included.

In this way, the application of pressure by the syringe can be adjusted by the operation of the pressure part, and the discharge rate of the adhesive from the discharge port can be adjusted.

The biological-tissue treating apparatus according to the present invention has an advantage in that, regardless of the type of biological tissue, a sufficient joining force can be quickly obtained, and the problem of adhesive becoming impossible to apply due to curing can be prevented.

DETAILED DESCRIPTION OF THE INVENTION

A biological-tissue processing apparatus 1 according to an embodiment of the present invention will be described below with reference to the drawings.

Figure 1:
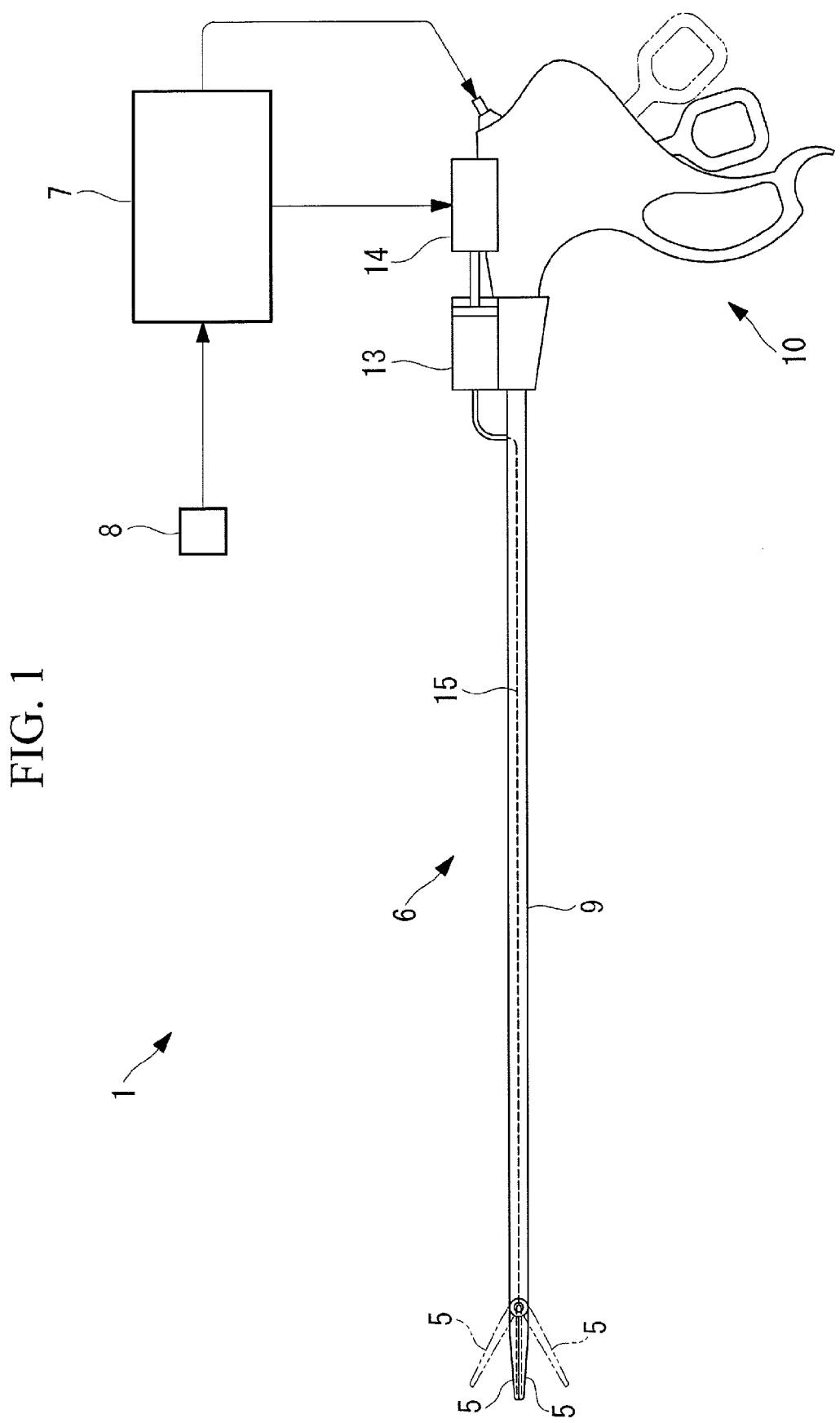
FIG. 1 is an overall structural diagram showing a biological-tissue joining apparatus according to an embodiment of the present invention.

The biological-tissue processing apparatus 1 of this embodiment, which is a biological-tissue joining apparatus (herein after also referred to as biological-tissue joining apparatus 1), is, as shown in FIG. 1, an apparatus for anastomosing biological tissue such as intestinal tracts 2 and 3, which are tubular biological tissue, as shown in FIGS. 6 to 11, and includes an apparatus main body 6 having a pair of electrodes 5 that clamp the intestinal tracts 2 and 3 from the outer radial direction so as to cover joined ends 2a and 3a of the pair of intestinal tracts 2 and 3, which are pressed together with a tubular anastomosing member 4 described below, a control unit 7 connected to the apparatus main body 6, and a switch 8 connected to the control unit 7.

The apparatus main body 6 includes the electrodes 5 provided at the tip, a thin rod 9 to be inserted into the body through an abdominal incision, and a handle 10 disposed at the base side of the rod 9 and configured to open and close the electrodes 5.

The electrodes 5 are attached to the tip of the rod 9 in such a manner that they pivot, in opposite directions from each other, around an axis orthogonal to the longitudinal direction of the rod 9 and are connected to the handle 10 provided at the base side of the rod 9 with a linking mechanism, not shown in the drawings. Thus, by operating the handle 10 at the base side of the rod 9 within the range illustrated with solid lines and broken lines in FIG. 1, the electrodes 5 provided at the tip of the rod 9 can be opened and closed.

Figure 2:
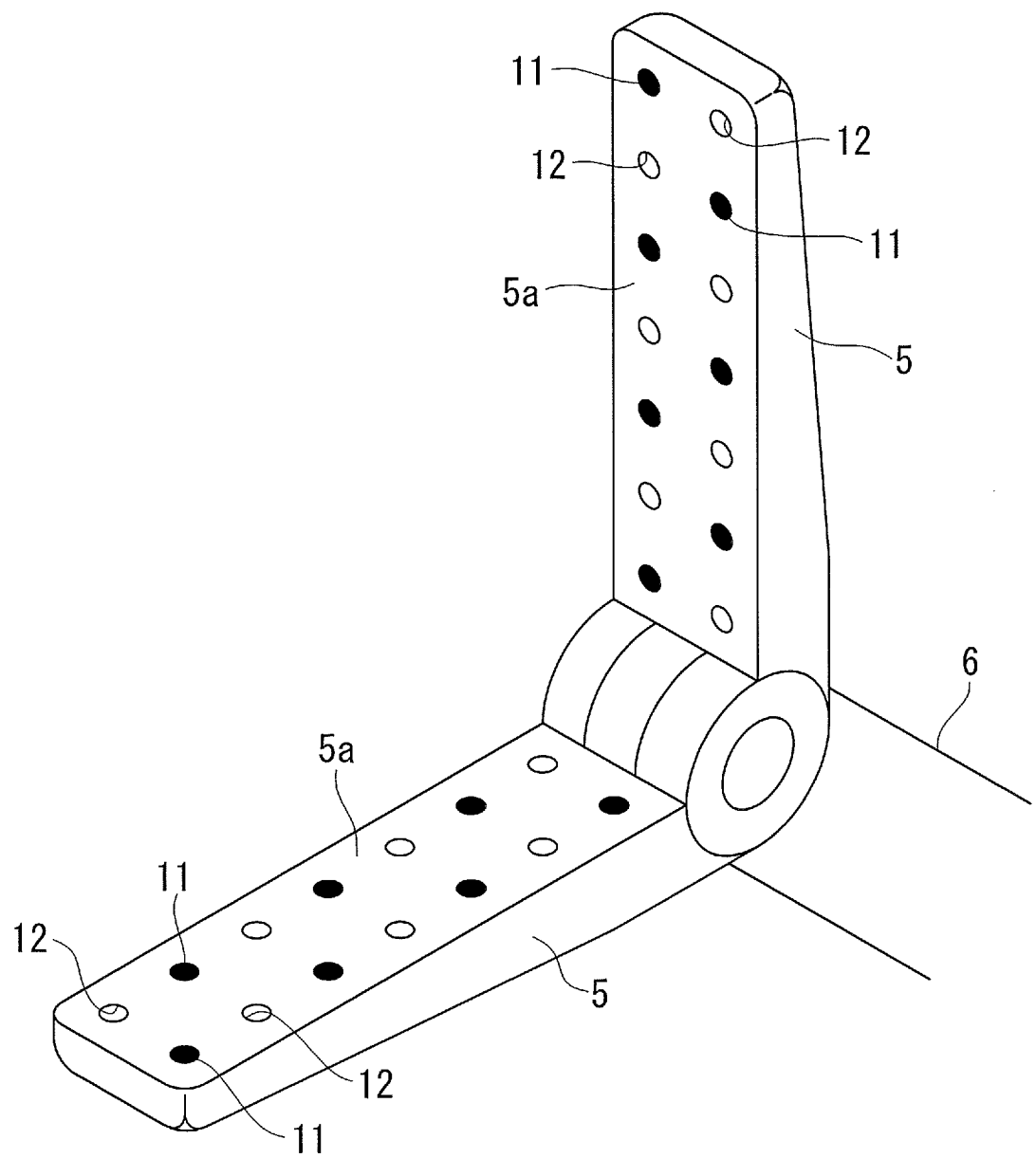
FIG. 2 is a perspective view illustrating opposing surfaces of electrodes of the biological-tissue joining apparatus in FIG. 1.

As shown in FIG. 2, a plurality of discharge ports 11 and 12 that respectively discharge collagen (adhesive) and elastin (adhesive), which are described below, are formed in opposing surfaces (contact surfaces) 5a of the pair of electrodes 5, i.e., the surfaces that are closely contacted with the external surfaces of the intestinal tracts 2 and 3 to be joined. The discharge ports 11 that discharge collagen and the discharge ports 12 that discharge elastin are alternately arranged and are capable of discharging collagen and elastin from the opposing surfaces 5a of the electrodes 5 in an even distribution.

As shown in FIG. 1, syringe-shaped tanks 13 that respectively accommodate collagen and elastin are provided at the base side of the rod 9 and are driven by a motor 14 (FIG. 1 shows only one of the tanks 13). The tanks 13 and the discharge ports 11 and 12 of the electrodes 5 are connected to tubes 15 disposed inside the rod 9. The collagen and elastin discharged from the tanks 13 are discharged respectively from the discharge ports 11 and 12 of the electrodes 5 through the tubes 15.

Figure 3:
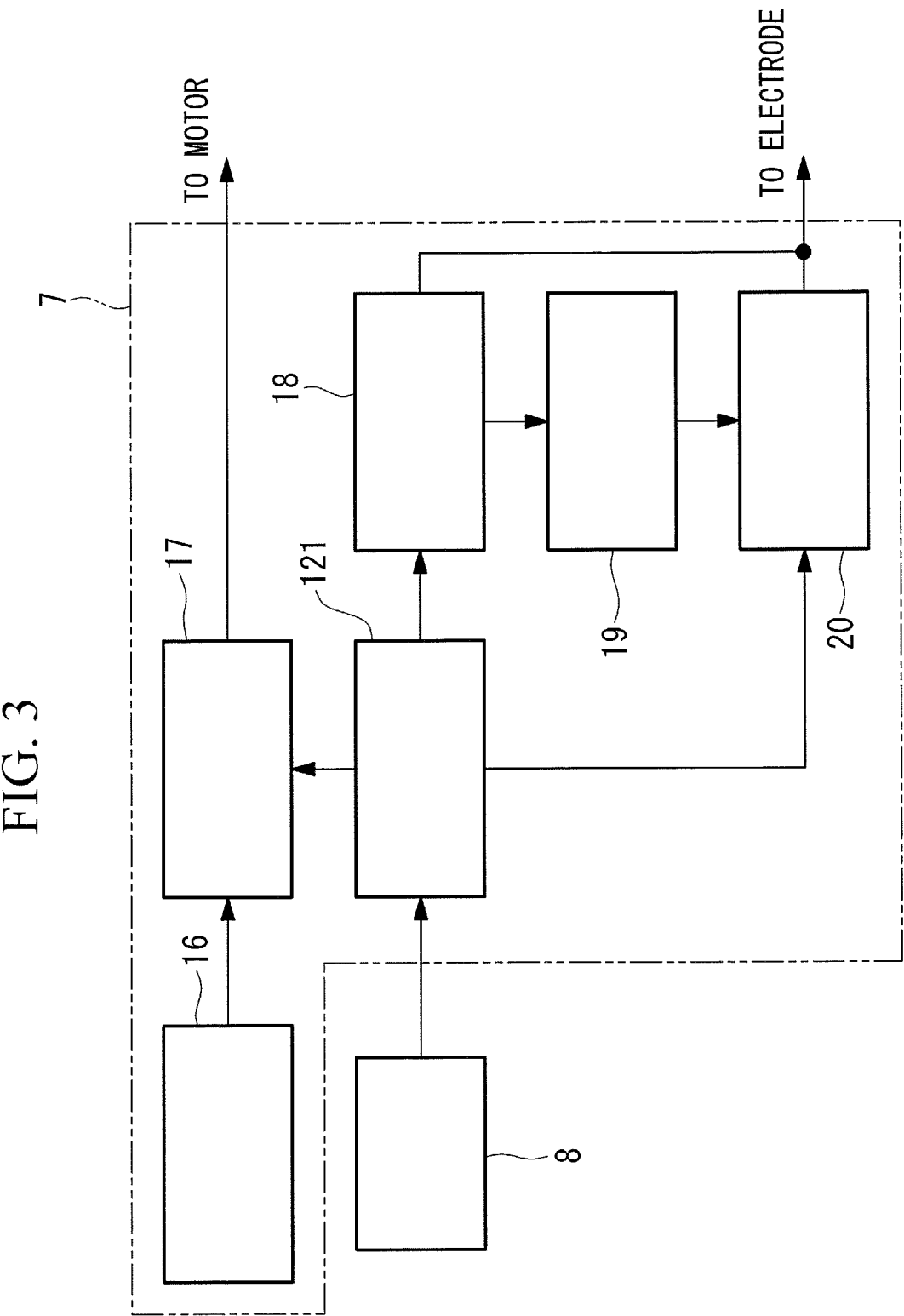
FIG. 3 is a block diagram illustrating a control unit of the biological-tissue joining apparatus in FIG. 1.

As shown in FIG. 3, the control unit 7 includes a discharge-rate setting unit 16 that sets the discharge rate of the collagen and elastin to be discharged, depending on the type of biological tissue to be joined; a discharge instruction unit 17 that outputs a discharge instruction signal corresponding to the discharge rate set by the discharge-rate setting unit 16 to the motor 14; a resistance measuring unit 18 that measures the resistance of the biological tissue to be joined by applying a weak voltage between the electrodes 5 before joining and then detecting the current flow; a voltage calculating unit 19 that calculates the voltage value at which the collagen and elastin, which are proteins contained in biological tissue, are melted, corresponding to the resistance measured by the resistance measuring unit 18; a voltage applying unit 20 that applies the voltage calculated by the voltage calculating unit 19 across the electrodes 5; and a control unit 121 that controls these components.

The switch 8 is, for example, a foot switch and applies a trigger input to the control section 121 provided in the control unit 7 by being pushed after preparation for the joining is completed by clamping the biological tissue with the electrodes 5. When a trigger is input from the switch 8, the control section 121 carries out the above-described operations of resistance detection, voltage value calculation, discharge of collagen and elastin, and voltage application in sequence.

Figure 4:
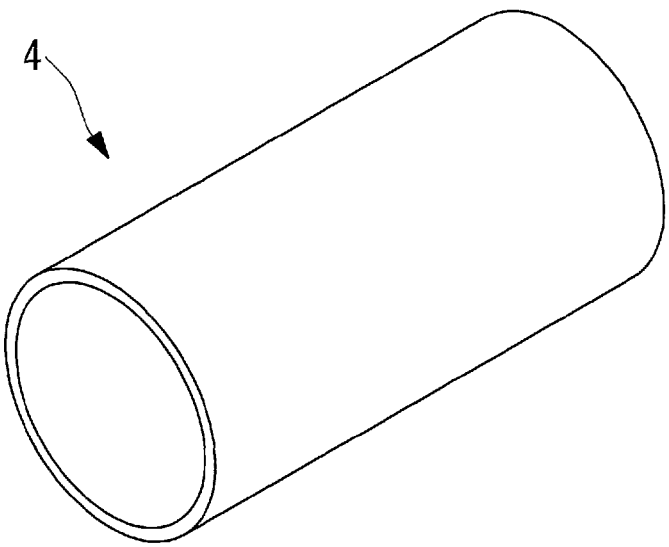
FIG. 4 is a perspective view illustrating an anastomosing member used for anastomosis of tubular biological tissue by the biological-tissue joining apparatus in FIG. 1.

As shown in FIG. 4, the anastomosing member 4 is a tubular member and is formed of a composite of polyaniline, polypyrrole, and polythiophene, or is formed of polylactic-acid-based polymers doped with carbon particles.

Figure 5A:
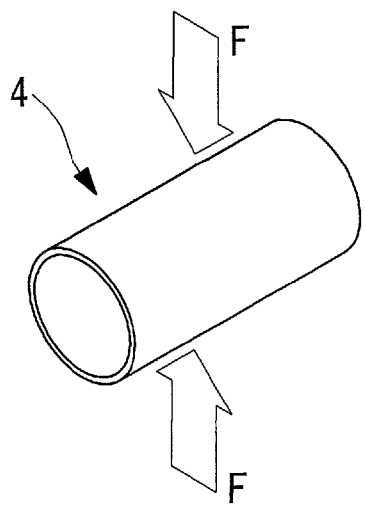
FIG. 5A is diagram for describing the flexibility of the anastomosing member in FIG. 4 and is a perspective view illustrating the shape before applying an external force.
Figure 5B:
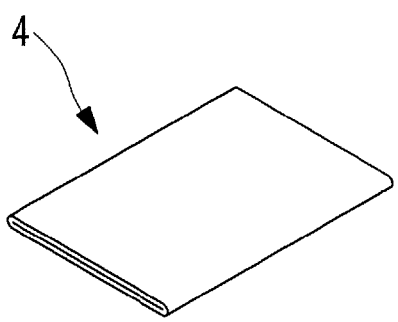
FIG. 5B is diagram for describing the flexibility of the anastomosing member in FIG. 4 and is a perspective view illustrating the shape after applying an external force.

By forming the anastomosing member 4 with polylactic-acid-based polymers, as shown in FIGS. 5A and 5B, the anastomosing member 4 has flexibility so as to prevent rupture even when its inner opening is closed and the inner surfaces come into close contact due to being crushed in the radial direction by external forces F. Furthermore, by forming the anastomosing member 4 with polylactic-acid-based polymers, the anastomosing member 4 has heat resistance so as to prevent deformation even when heated to a temperature higher than the melting point of collagen.

By forming the anastomosing member 4 with polylactic-acid-based polymers, the anastomosing member 4 has resilience so as to restore the closed inner opening when the external forces F are released after it is heated to a temperature higher than the melting point of collagen in a crushed state due to the external forces F.

Furthermore, the anastomosing member 4 has electrical conductivity by forming it of a composite of polyaniline, polypyrrole, and polythiophene or by doping carbon particles. In this embodiment, for example, the electrical conductivity is sufficiently high such that the resistance is sufficiently lower than the biological tissue to be joined.

The operation of the biological-tissue joining apparatus 1 of this embodiment, having such a configuration, will be described below.

A case in which the biological-tissue joining apparatus 1 of this embodiment is used to join biological tissue, such as the tubular intestinal tracts 2 and 3, will be described.

First, the supply rates of collagen and elastin predetermined for each type of biological tissue are set by the discharge-rate setting unit 16 of the control unit 7. The setting of the supply rates may be carried out by selecting the type of biological tissue or by directly inputting the supply rates of collagen and elastin.

Figure 6:
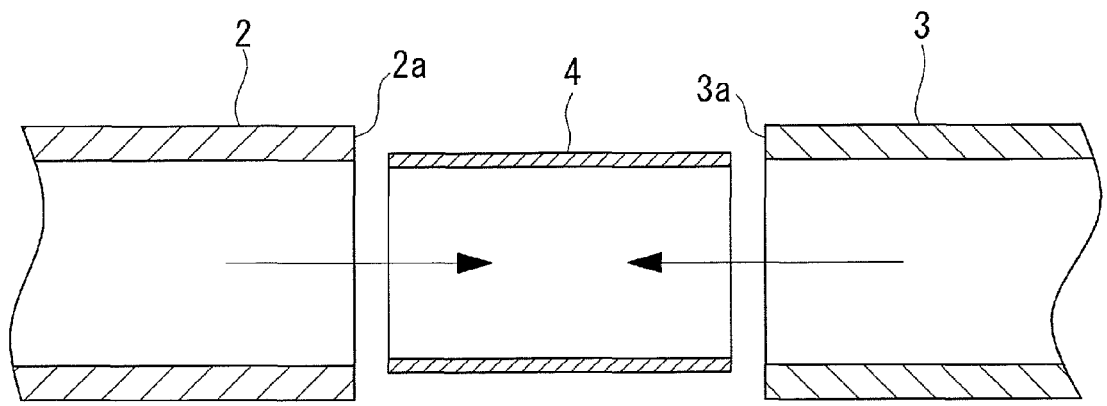
FIG. 6 is a longitudinal sectional view illustrating the procedure of anastomosis of a pair of intestinal tracts by the anastomosing member in FIG. 4.
Figure 7:
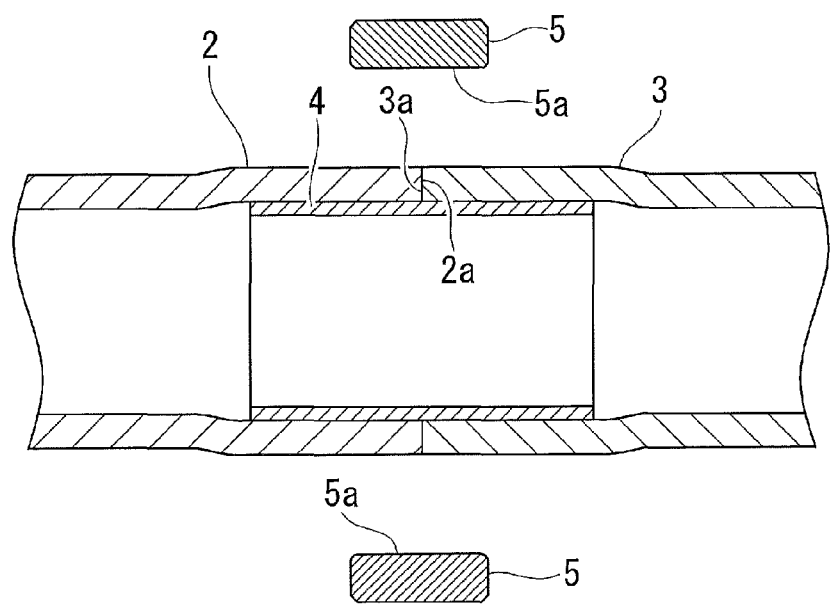
FIG. 7 is a longitudinal sectional view illustrating a state after the state in FIG. 6, in which the anastomosing member is inserted into end openings of the intestinal tracts and the joining edges of the intestinal tracts are put against each other.

Next, as shown in FIG. 6, the anastomosing member 4 of this embodiment is inserted into the openings of the joined ends 2a and 3a of the pair of intestinal tracts 2 and 3 to be joined in order to press together the joined ends 2a and 3a of the pair of intestinal tracts 2 and 3, as shown in FIG. 7. As shown in FIG. 7, in this state, by moving the pair of electrodes 5 disposed at the tip of the apparatus main body 6 of the biological-tissue joining apparatus 1 of this embodiment close together in the outer radial direction in the proximity of the joined ends 2a and 3a and operating the handle 10, the intestinal tracts 2 and 3 and the anastomosing member 4 are clamped by the external forces F in the radial direction, as shown in FIG. 8.

Figure 8:
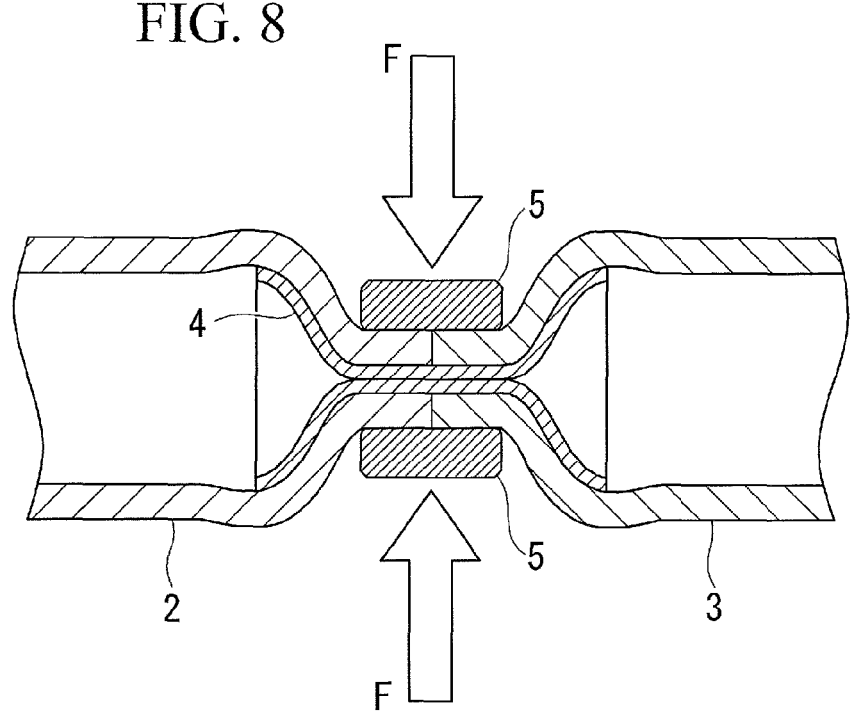
FIG. 8 is a longitudinal sectional view illustrating a state after the state in FIG. 7, in which the intestinal tracts and the anastomosing member are pressed in the radial direction by the electrodes.

Since the anastomosing member 4 has flexibility, as shown in FIG. 8, the anastomosing member 4 can be crushed until the inner opening is closed and the inner surfaces are placed in close contact by the external forces F. In this state, by pushing the switch 8 connected to the control unit 7, the operation of the control section 121 first causes the resistance measuring unit 18 to be operated and then the resistance of the intestinal tracts 2 and 3 clamped with the electrodes 5 is measured, and the voltage calculating unit 19 is operated to calculate the value of the voltage to be applied. Then, the control section 121 operates the voltage applying unit 20 to apply the voltage calculated by the voltage calculating unit 19 across the electrodes 5.

Figure 9:
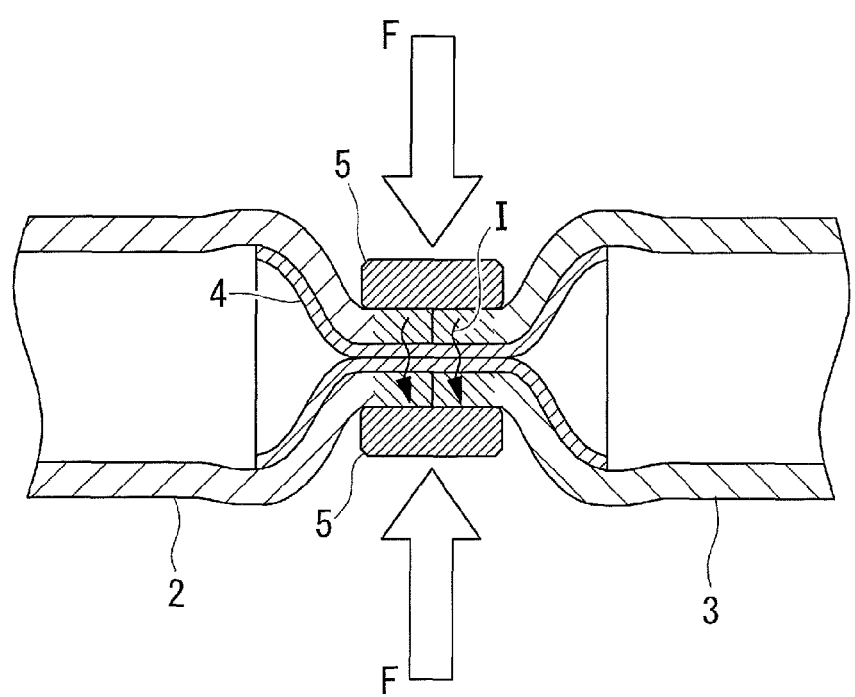
FIG. 9 is a longitudinal sectional view illustrating a state after the state in FIG. 8, in which electricity is applied to the intestinal tracts and the anastomosing member by the electrodes.

Since the anastomosing member 4 has electrical conductivity, as shown in FIG. 9, a current I flows through the intestinal tracts 2 and 3 and the anastomosing member 4 between the electrodes 5, and heat is generated at an amount proportional to the product of the magnitude of the resistance of the intestinal tracts 2 and 3 and the magnitude of the current I squared.

In such a case, because the anastomosing member 4 of this embodiment has high electrical conductivity such that the resistance is sufficiently smaller than the resistance of the intestinal tracts 2 and 3, the amount of heat generated at the anastomosing member 4 due to applying electricity is small, and energy is not wasted. Furthermore, since the anastomosing member 4 has heat resistance higher than the melting temperature of collagen, it does not deteriorate and is capable of maintaining its properties even when heated to a temperature that melts collagen.

Figure 10:
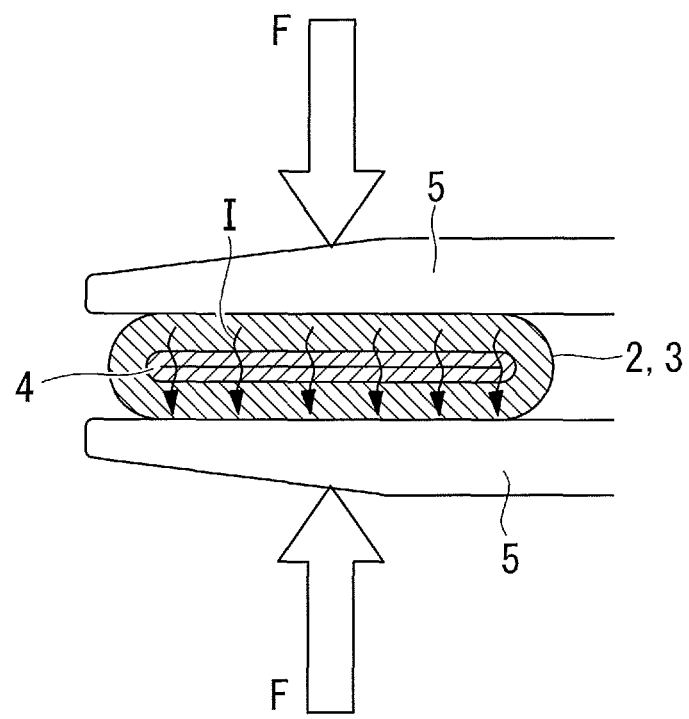
FIG. 10 is a lateral sectional view illustrating the anastomosing member in the state in FIG. 9, viewed from the axial direction thereof.

Then, by adjusting the voltage applied across the electrodes 5 by the voltage calculating unit 19 such that its temperature is slightly higher than the melting temperature of collagen due to the heat generated in the intestinal tracts 2 and 3, the collagen and elastin, which form the extracellular matrix contained in the intestinal tracts 2 and 3, can be melted to have good fluidity. Then, the collagen having fluidity due to heat seeps in to the gaps between the intestinal tracts 2 and 3 and the anastomosing member 4. As shown in FIG. 10, since this occurs around the entire circumference of the anastomosing member 4, the fluid collagen seeps into the entire peripheral surface of the anastomosing member 4.

In such a case, with the biological-tissue joining apparatus 1 of this embodiment, before applying a voltage across the electrodes 5, a discharge instruction signal is output from the discharge instruction unit 17 to the motor 14, and collagen and elastin are discharged toward the biological tissue at discharge rates corresponding to the type of biological tissue.

Therefore, even when the amount of collagen and elastin contained in the biological tissue is small, the amount of collagen can be supplemented to a necessary and sufficient level for joining of the tissue, or hardening of the biological tissue due to loss of elastin can be prevented.

As a result, there are advantages in that the supply of collagen generates a stable joining force, and flexibility of the biological tissue can be maintained after joining.

Figure 11:
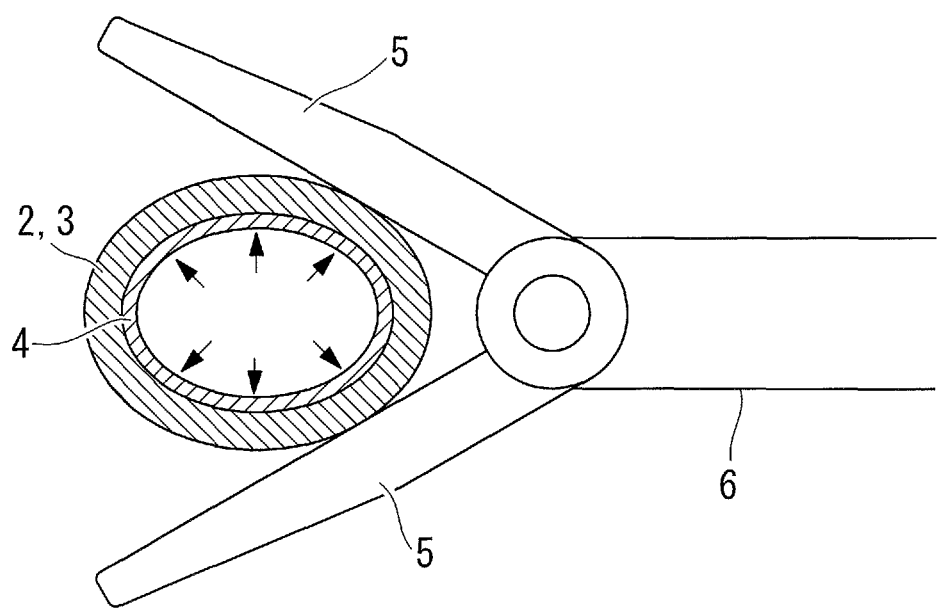
FIG. 11 is a lateral sectional view illustrating the state after the state in FIG. 10, in which the electricity application is stopped and the pressure is released.

In this state, the voltage applied to the electrodes 5 is stopped, and, as shown in FIG. 11, the external forces F applied to the electrodes 5 are released. Since the anastomosing member 4 is resilient, when the external forces F are released, the anastomosing member 4 is restored in such a manner that it spreads in the outer radial direction and opens the inner opening.

In other words, on the peripheral surface of the anastomosing member 4, the collagen that seeped in between the intestinal tracts 2 and 3 and the anastomosing member 4 functions as an adhesive to adhere the intestinal tracts 2 and 3 and the anastomosing member 4. On the other hand, because no collagen that can be used as an adhesive is present on the inner surface of the anastomosing member 4, the inner surfaces in close contact are not adhered but are separated by the resilience of the anastomosing member 4 when the external forces F are released, and are opened.

Figure 12:
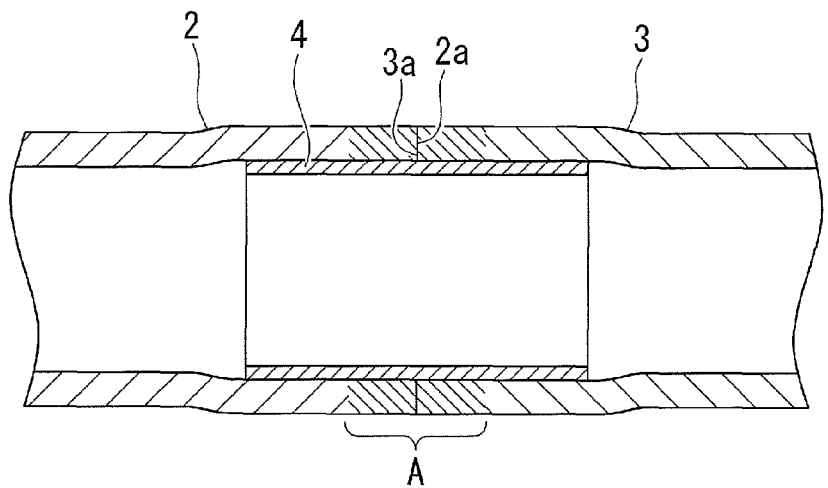
FIG. 12 is a longitudinal sectional view illustrating the pair of intestinal tracts integrated by anastomosis using the biological-tissue joining apparatus in FIG. 1 and the anastomosing member in FIG. 4.
Figure 13:
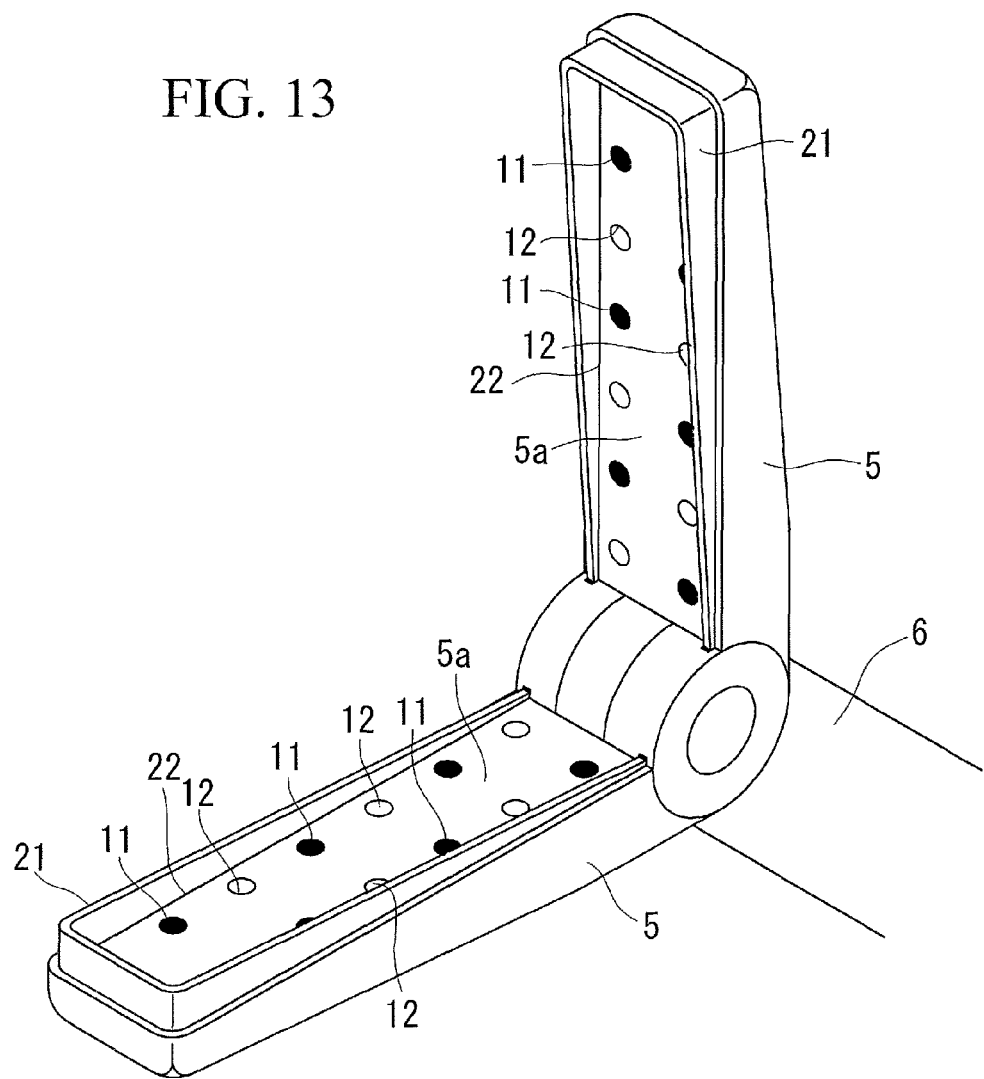
FIG. 13 is a partial perspective view showing a modification of the biological-tissue joining apparatus in FIG. 1.

In this way, as shown in FIG. 12, the joined ends 2a and 3a of the pair of intestinal tracts 2 and 3 are pressed together and joined to be integrated in a state in which regions A in the proximity of the joined ends of the intestinal tracts 2 and 3 clamped with the electrodes 5 and the anastomosing member 4 disposed inward in the radial direction are adhered along the entire circumference.

In other words, with the biological-tissue joining apparatus 1 of this embodiment, the intestinal tracts 2 and 3, which are a pair of tubular biological tissues, can be easily anastomosed at once merely by applying a voltage while clamping them with the pair of electrodes 5 with the predetermined external forces F.

As a result, there is an advantage in that the operation is significantly simplified compared with conventional anastomosis by suturing or anastomosis by applying ultrasound a plurality of times in the circumferential direction. In particular, with endoscopic surgery carried out in a space not sufficient for handling energy therapy equipment, there is an advantage in that the complexity of the anastomosis operation is significantly reduced since just a space sufficient for clamping the intestinal tracts 2 and 3 once in the radial direction is required.

With the biological-tissue joining apparatus 1 of this embodiment, since collagen and elastin are discharged from the discharge ports 11 and 12 provided in the opposing surfaces 5a of the electrodes 5, collagen and elastin can be supplied to only the regions that require joining, in a state with the regions that require joining being clamped with the electrodes 5. In other words, unlike a method of applying or spraying collagen and elastin onto the joining regions in advance, problems such as dripping and attaching of collagen and elastin onto the surrounding tissue can be prevented.

Since the anastomosing member 4 is adhered to the inner walls of the intestinal tracts 2 and 3 with collagen, there is an advantage in that the anastomosis state can be stably maintained compared with conventional anastomosing members secured only by means of friction. Moreover, since the anastomosing member 4 is composed of polylactic-acid-based polymers, which have high biodegradability, after anastomosis surgery, it decomposes and disappears over time. In other words, it is advantageous in that, when the anastomosed region A heals by joining together, the anastomosing member 4 of this embodiment disappears without leaving any foreign objects inside the body.

The biological tissue joined by the biological-tissue joining apparatus 1 of this embodiment is not limited to the intestinal tracts 2 and 3 and may be any tubular biological tissue, such as other digestive tracts, blood vessels, or a ureter, or may be any flat biological tissue, such as skin.

In the description of this embodiment, the intestinal tracts 2 and 3 are joined with the tubular anastomosing member 4 being provided therebetween. Instead, however, the form of the anastomosing member 4 is not limited thereto, and joining may be carried out without using the anastomosing member 4.

In this embodiment, as energy supplied to the biological tissue, electrical energy is supplied from the electrodes 5. Instead, however, ultrasonic vibration may be supplied by contacting an ultrasonic transducer.

Figure 14:
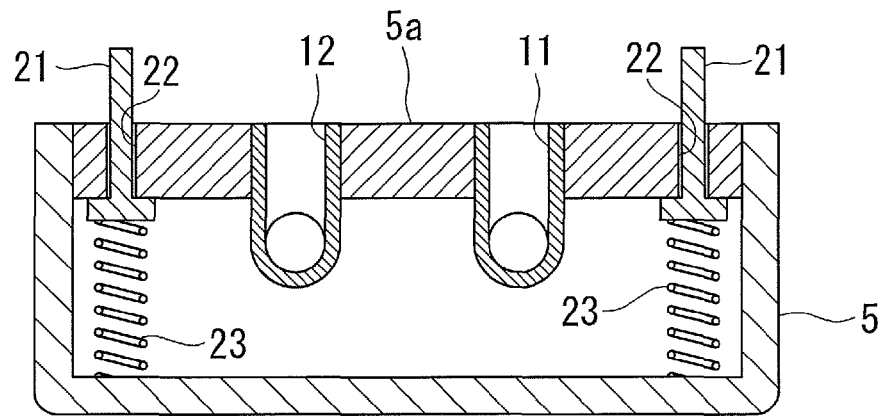
FIG. 14 is a lateral sectional view illustrating the internal structure of an electrode in FIG. 13.

With this embodiment, as shown in FIGS. 13 to 16, it is preferable that peripheral-wall members (leakage preventing parts) 21 be provided in the peripheral section of the opposing surfaces 5a of the electrodes 5 of the main body 6 so as to surround the discharge ports 11 and 12 provided in the opposing surfaces 5a. As shown in FIG. 14, the peripheral-wall members 21 are accommodated, in such a manner that they are capable of appearing therefrom, inside slits 22 provided in the opposing surfaces 5a and are biased in a direction projecting from the opposing surfaces 5a by spring members (driving parts) 23 provided in the electrodes 5.

Figure 15:
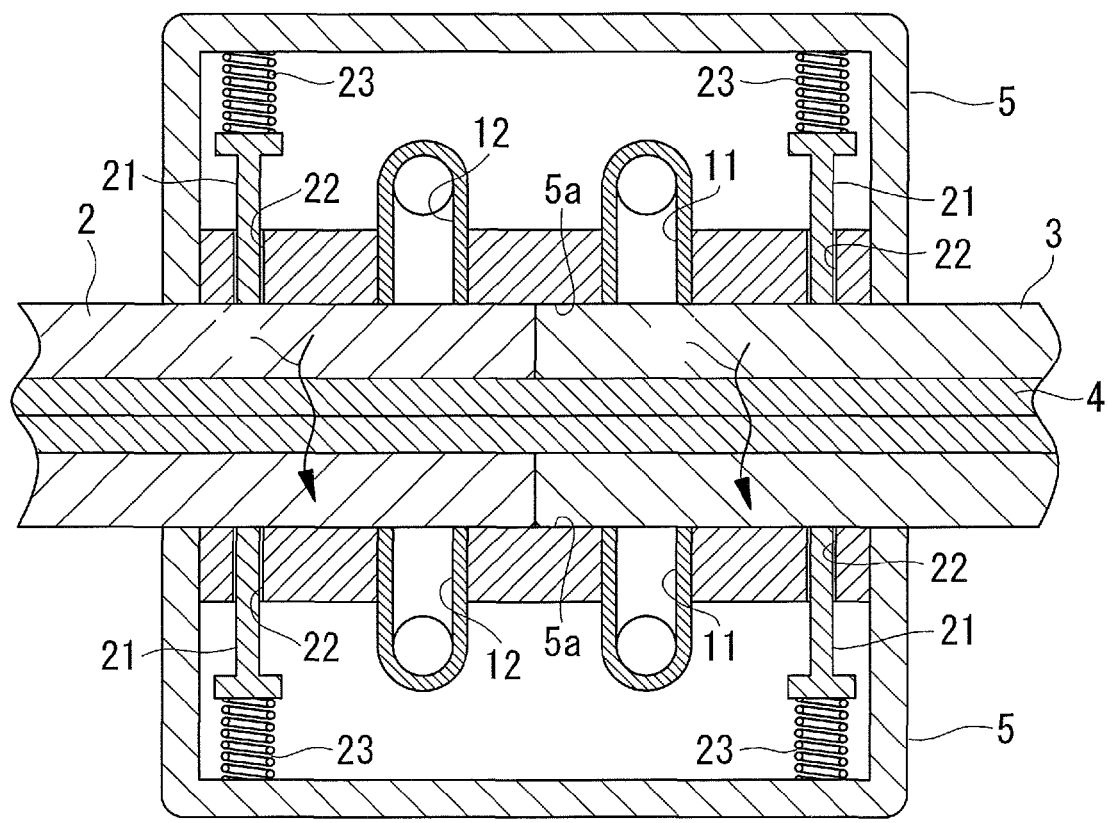
FIG. 15 is a lateral sectional view illustrating a state in which the biological tissue is clamped and electricity is applied by the electrodes in FIG. 13.
Figure 16:
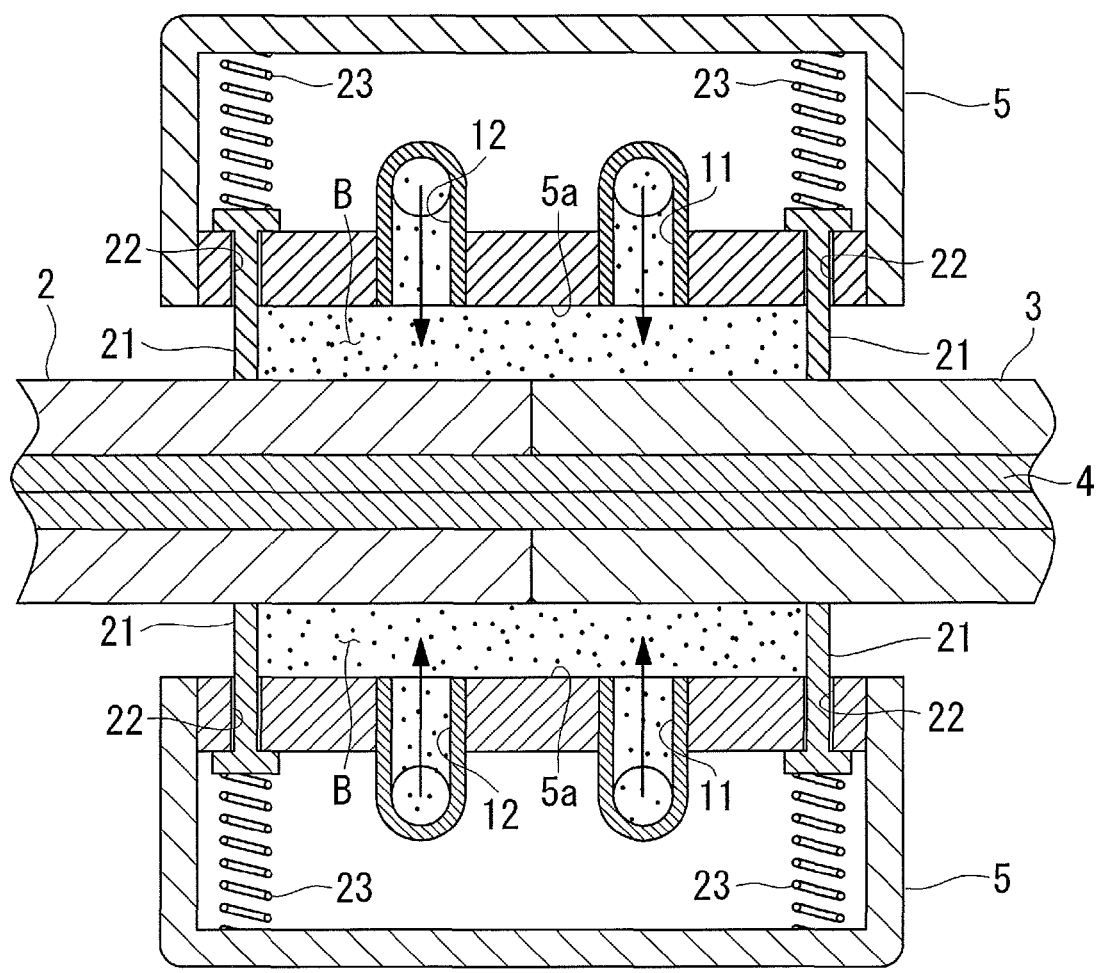
FIG. 16 is a lateral sectional view illustrating a state after the state in FIG. 15, in which an adhesive is discharged from discharge ports provided in the opposing surfaces of the electrodes.

In this way, as shown in FIG. 15, when the electrodes 5 are closed together and the intestinal tracts 2 and 3 are clamped with the opposing surfaces 5a, the peripheral-wall members 21 are accommodated inside the slits 22 by being pushed against the biasing force of the spring members 23 by the surfaces of the intestinal tracts 2 and 3 and make the opposing surfaces 5a closely contact the surface of the intestinal tracts 2 and 3 so as to cause the current I to flow. On the other hand, as shown in FIG. 16, when the electrodes 5 are moved apart and the moved away from the surface of the intestinal tracts 2 and 3, the peripheral-wall members 21 protrude from the slits 22 of the opposing surfaces 5a by the biasing force of the spring members 23, and the contact with the surface of the intestinal tracts 2 and 3 is maintained.

In other words, since the peripheral-wall members 21 surrounding the outside of the discharge ports 11 and 12 are closely contacted to the surfaces of the intestinal tracts 2 and 3 in either a state in which the intestinal tracts 2 and 3 are clamped with the opposing surfaces 5a of the electrodes 5 or a state in which the opposing surfaces 5a of the electrodes 5 are slightly separated from the surfaces of the intestinal tracts 2 and 3, an adhesive B, such as collagen and elastin discharged from the discharge ports 11 and 12, is prevented from leaking to the outside from the peripheral-wall members 21.

In this way, the problem of the uncured adhesive B bonding peripheral tissue outside the joining site can be prevented.

Since the peripheral-wall members 21 are provided on the opposing surfaces 5a in such a manner that they are capable of appearing and are biased in a protruding direction by the spring members 23, when electricity is applied by closely contacting the opposing surfaces 5a of the electrodes 5, the peripheral-wall members 21 retract into the opposing surfaces 5a and do not disturb the close contact of the opposing surfaces 5a. Furthermore, when the external forces F applied to the electrodes 5 are released and a gap is formed between the opposing surfaces 5a, the peripheral-wall members 21 protrude from the opposing surfaces 5a by the spring members 23, the close contact of the intestinal tracts 2 and 3 is maintained, and the adhesive B is continuously prevented from leaking outside.

Figure 17:
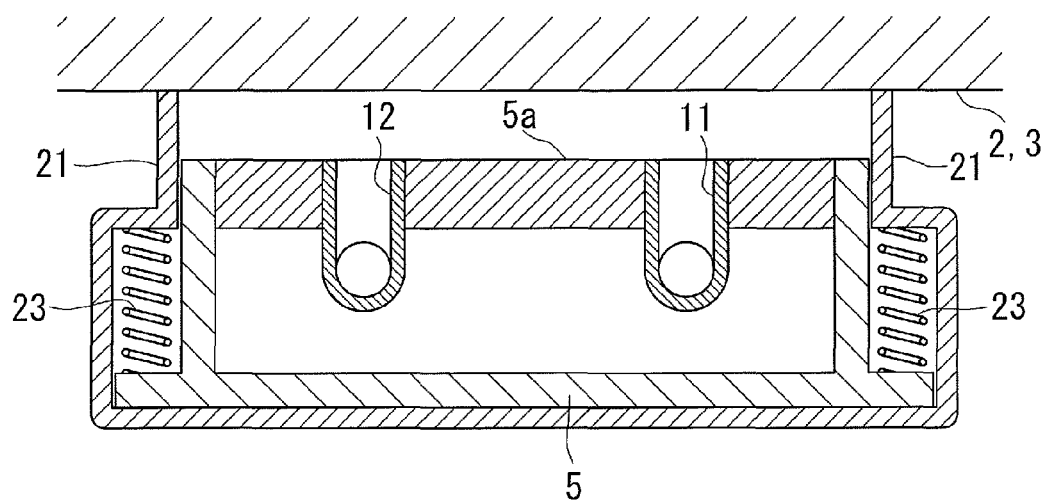
FIG. 17 is a partial lateral sectional view illustrating electrodes in another modification of the biological-tissue joining apparatus in FIG. 1.
Figure 18:
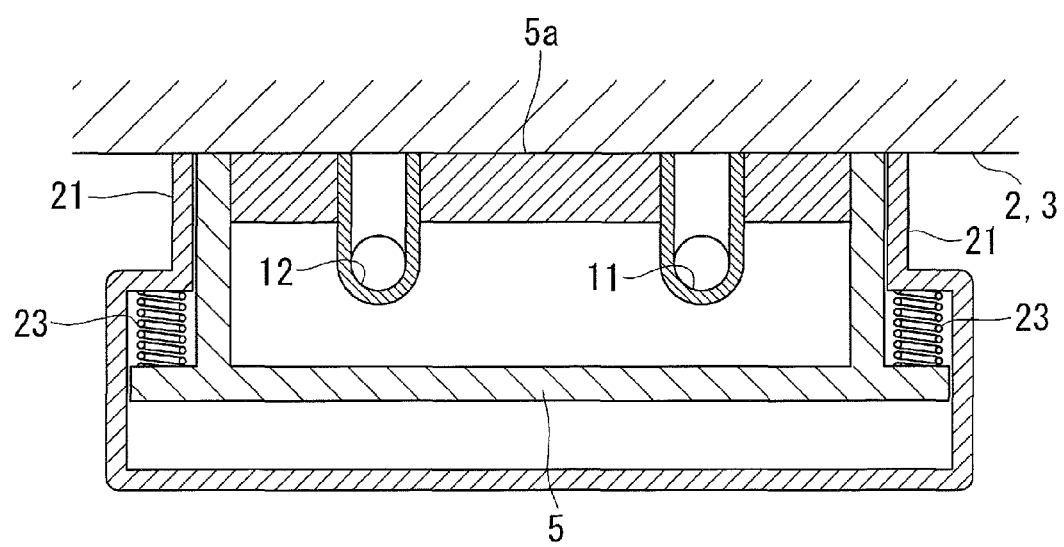
FIG. 18 is a lateral sectional view illustrating a state in which the electrodes in FIG. 17 are pressed against biological tissue.

As described above, by providing the slits 22 in the opposing surfaces 5a of the electrodes 5, the peripheral-wall members 21 appear from the slits 22, where they were accommodated. Instead, however, as shown in FIGS. 17 and 18, box-shaped peripheral-wall members 21 that cover the entire electrodes 5 may be used. In such a case, as shown in FIG. 17, by biasing the ends of the peripheral-wall members 21 by the spring members 23 in a direction protruding relative to the opposing surfaces 5a of the electrodes 5, the peripheral-wall members 21 can be closely contacted with the surfaces of the intestinal tracts 2 and 3 either in a state in which the electrodes 5 are in close contact (electrically conductive) or in a state with a slight gap between the electrodes 5 (electrically non-conductive); thus, the adhesive B discharged from the discharge ports 11 and 12 can be prevented from leaking outside.

Figure 19:
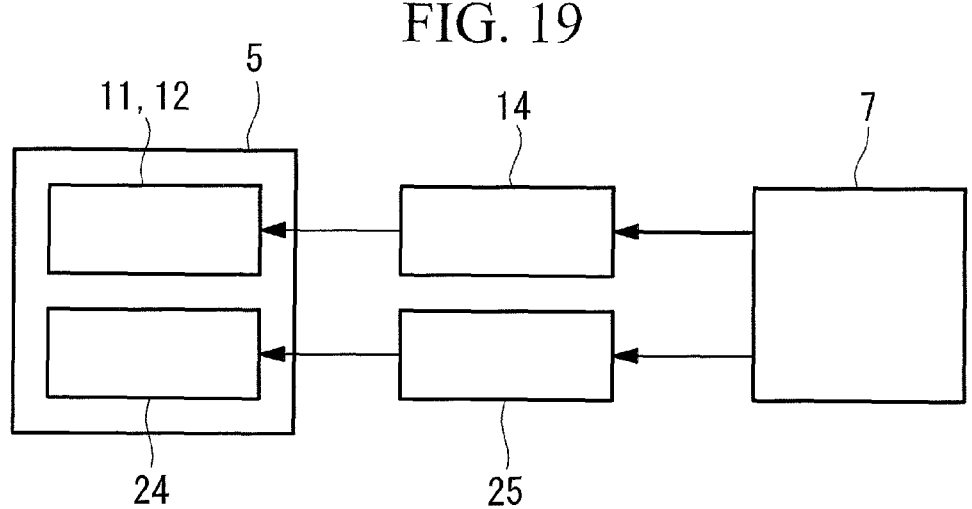
FIG. 19 is a block diagram illustrating another modification of the biological-tissue joining apparatus in FIG. 1.
Figure 20:
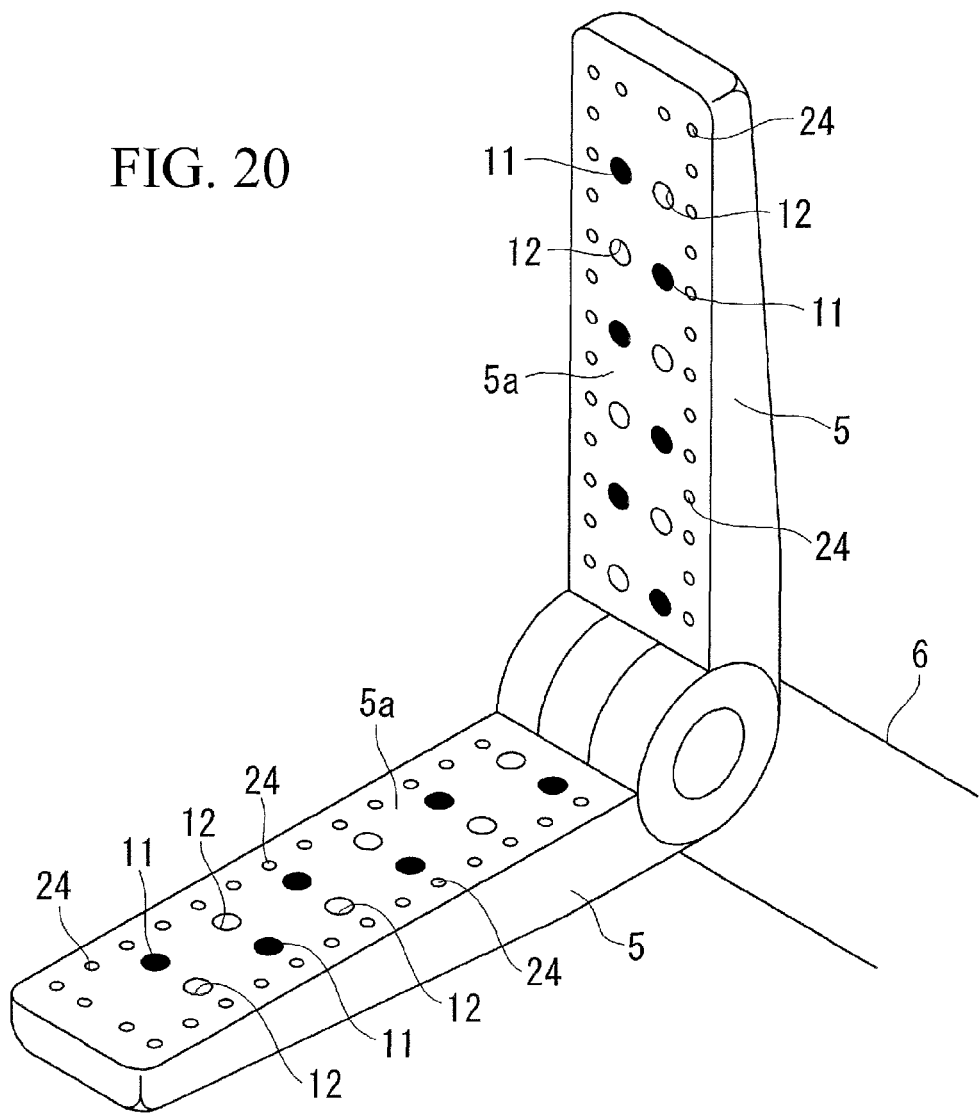
FIG. 20 is a partial perspective view illustrating electrodes of the biological-tissue joining apparatus in FIG. 19.

Instead of the leakage preventing parts that prevent leakage of collagen and elastin by the peripheral-wall members 21, as shown in FIGS. 19 and 20, suction ports 24 formed in the opposing surfaces 5a and a suction pump (negative-pressure supplying part) 25 that evacuates the suction ports 24 to negative pressure may be provided. In such a case, as shown in FIG. 20, it is preferable that the suction ports 24 be disposed in positions surrounding the outside of the discharge ports 11 and 12. In this way, even when the amount of collagen and elastin discharged from the discharge ports 11 and 12 is too large, the suction pump 25 can be operated to evacuate the suction ports 24 to negative pressure; thus, the excess collagen and elastin can be removed. In this way, collagen and elastin can be prevented from leaking from between the opposing surfaces 5a.

Figure 21:
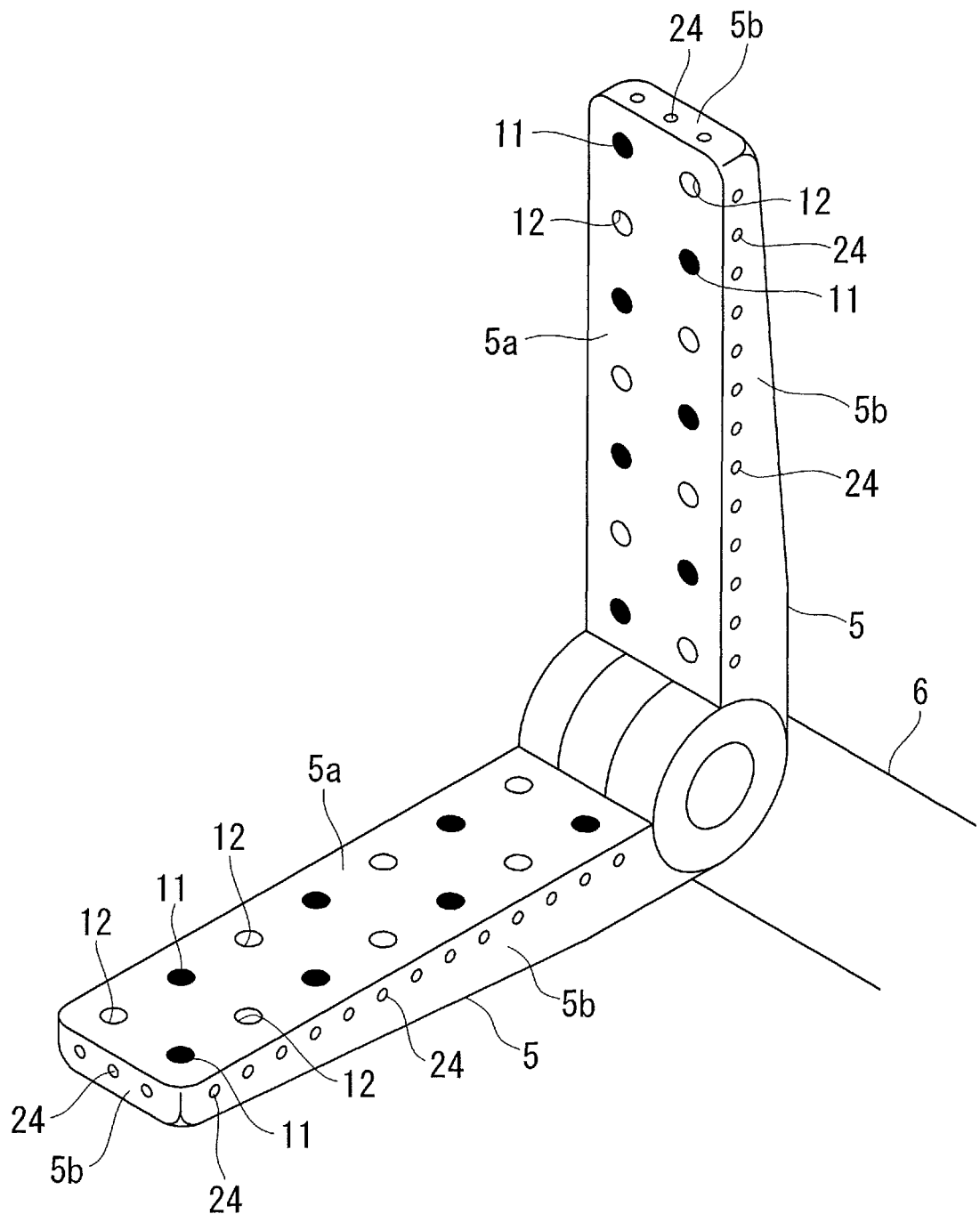
FIG. 21 is a partial perspective view illustrating a modification of the electrodes of the biological-tissue joining apparatus in FIG. 19.

The suction ports 24 may be formed in the opposing surfaces 5a but also, as shown in FIG. 21, may be provided on side surfaces 5b adjacent to the opposing surfaces 5a. In this way, by operating the suction pump 25 and evacuating the suction ports 24 to negative pressure, collagen and elastin that would otherwise flow outside through the gaps between the opposing surfaces 5a are sucked through the suction ports 24, thus preventing further leakage.

Figure 22:
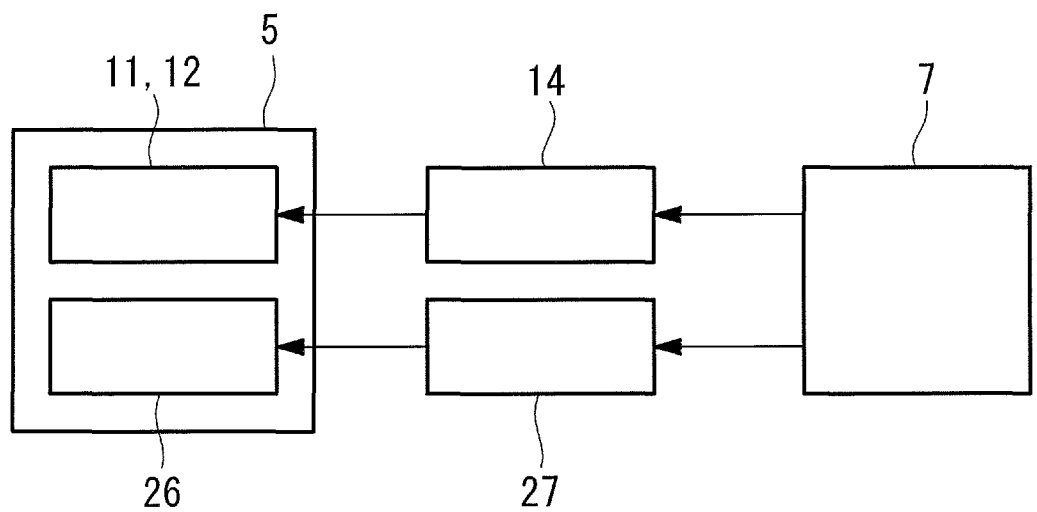
FIG. 22 is a block diagram illustrating another modification of the biological-tissue joining apparatus in FIG. 1.

As shown in FIG. 22, instead of the suction ports 24 shown in FIGS. 19 to 21, washing-solution discharge ports 26 may be used, and instead of the suction pump 25, a washing-solution pump 27 may be used. As the washing solution, for example, normal saline, lactated Ringer's solution, or phosphate buffered saline may be used. In this way, the washing solution is discharged from the washing-solution discharge ports 26 by the operation of the washing-solution pump 27, and thus excess collage and elastin can be washed away. In other words, by lowering the concentration of collagen and elastin, the adhesive force is lowered, thus preventing adherence of the collagen and elastin to other tissue in the event of leakage. In such a case, washing-solution suction ports (not shown) may be provided in positions surrounding the washing-solution discharge ports 26 to remove the excess washing solution by suction.

In each embodiment described above, collagen and elastin are discharged from the discharge ports 11 and 12. Instead, however, other adhesives may be discharged. The adhesive may be a one-component or two-component adhesive. The adhesive may be cured by a chemical reaction, or may have a property in which curing occurs by a physical stimulus, such as heat, light, or ultrasound.

Figure 23:
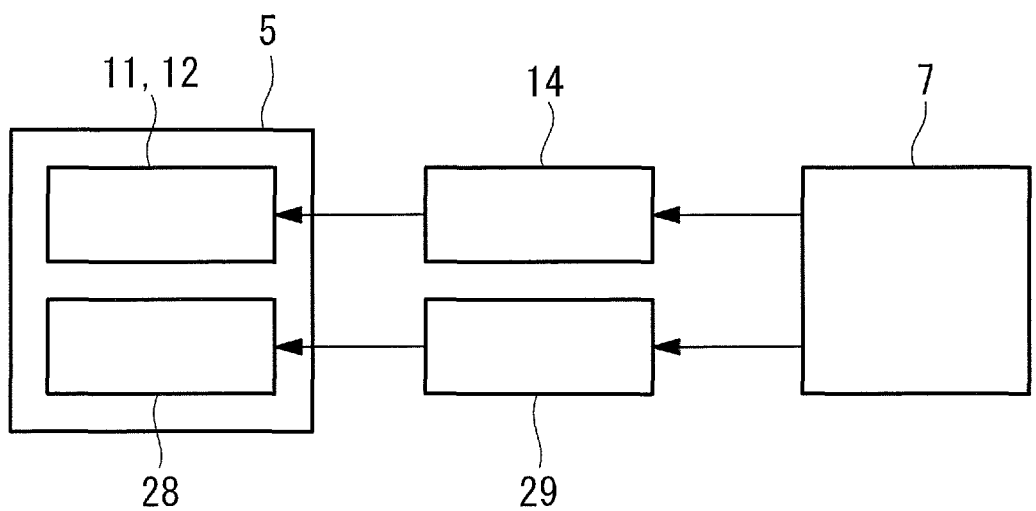
FIG. 23 is a block diagram illustrating another modification of the biological-tissue joining apparatus in FIG. 1.

When an adhesive that is cured by a physical stimulus is used, as shown in FIG. 23, the leakage preventing part may be formed by providing energy supplying parts 28 on the electrodes 5, and energy supplying parts 29 that supply energy to the energy supplying parts 28 may be connected thereto.

Figure 24:
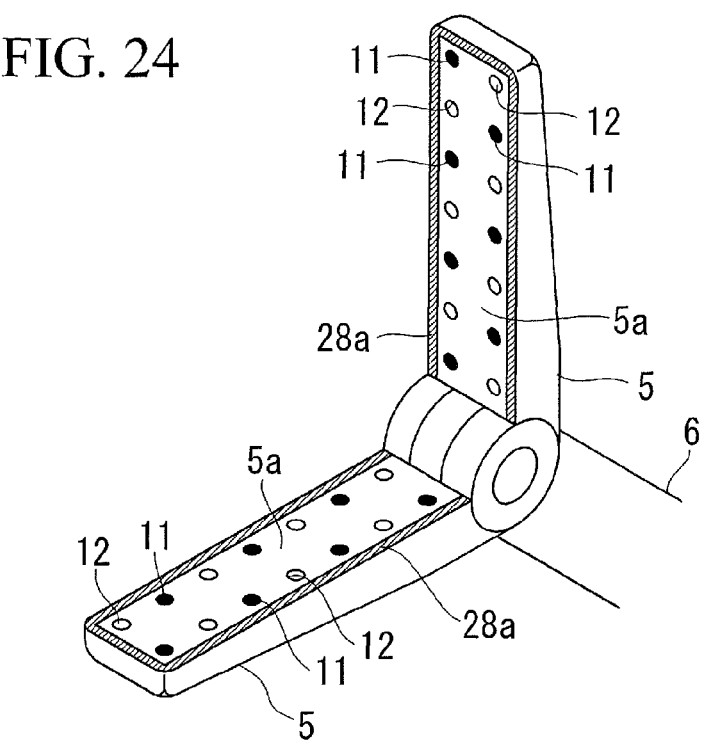
FIG. 24 is a partial perspective view illustrating the electrodes of the biological-tissue joining apparatus in FIG. 23.
Figure 25:
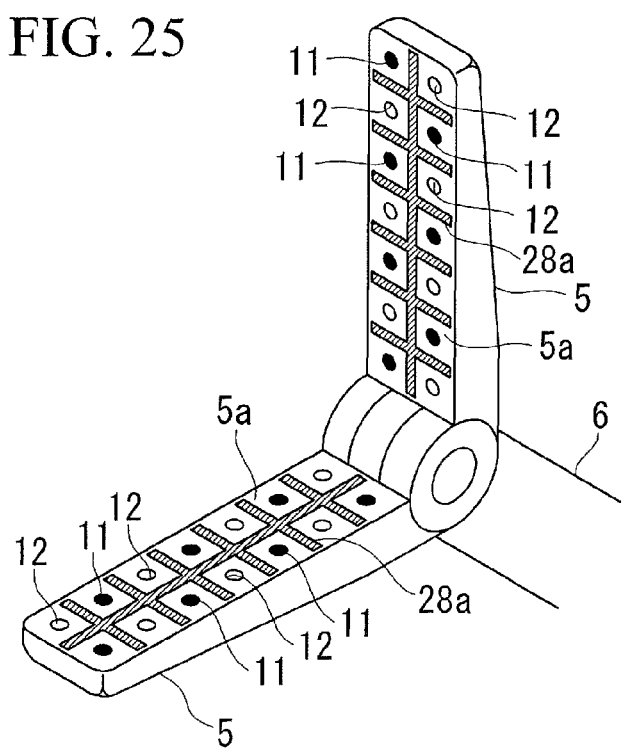
FIG. 25 is a partial perspective view illustrating a modification of the electrodes of the biological-tissue joining apparatus in FIG. 23.

In other words, when discharging an adhesive that is cured by applying heat, as shown in FIGS. 24 and 25, heaters 28a may be provided on the opposing surfaces 5a to heat the discharged adhesive. FIG. 24 illustrates an example in which the heaters 28a are provided at the peripheral sections of the opposing surfaces 5a. FIG. 25 illustrates an example in which the heaters 28a are provided between all of the discharge ports 11 and 12 in the opposing surfaces 5a.

Figure 26:
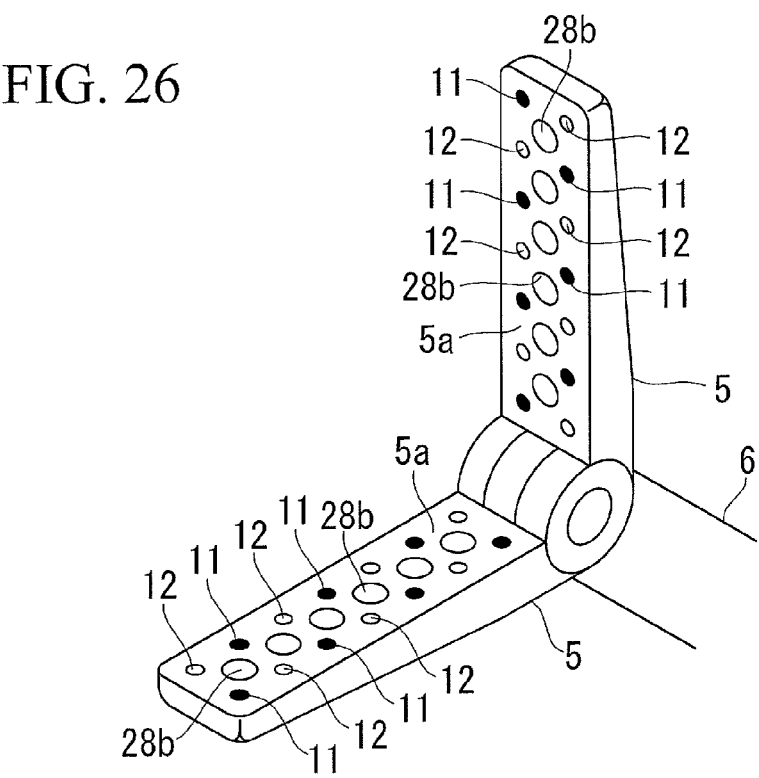
FIG. 26 is a partial perspective view illustrating a modification of the electrodes of the biological-tissue joining apparatus shown in FIG. 23.
Figure 27:
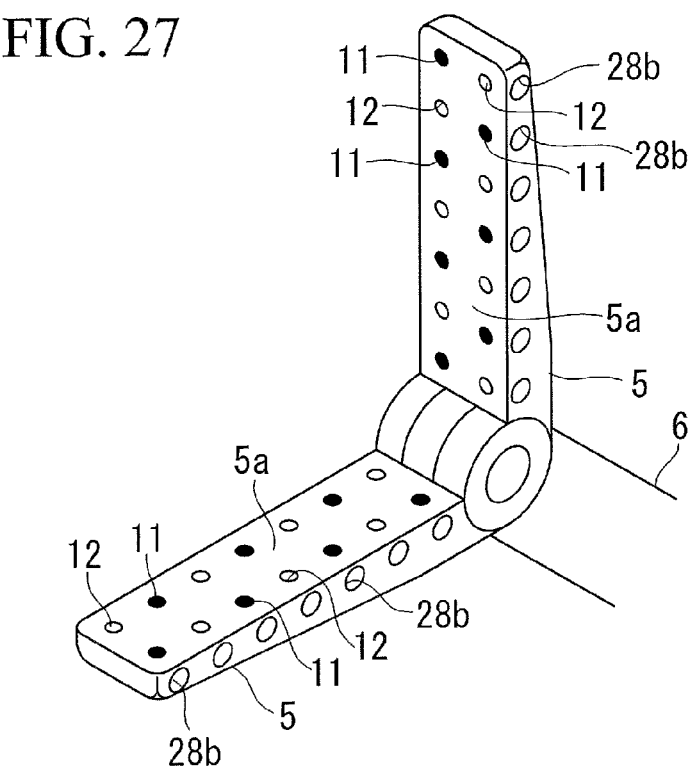
FIG. 27 is a partial perspective view illustrating a modification of the electrodes of the biological-tissue joining apparatus in FIG. 23.

When an adhesive that is cured by being irradiated with light is discharged, as shown in FIGS. 26 and 27, light-projecting parts 28b that emit light to the opposing surfaces 5a may be provided to irradiate the discharged adhesive with light. The light-projecting parts 28b may be light sources that generate light or may be tips of light-conducting members, such as optical fibers, that guide light. FIG. 26 illustrates an example in which the light-projecting parts 28b are provided between the discharge ports 11 and 12 in the opposing surfaces 5a. FIG. 27 illustrates an example in which the light-projecting parts 28b are provided in the side surfaces 5b adjacent to the opposing surfaces 5a of the electrodes 5.

Figure 28:
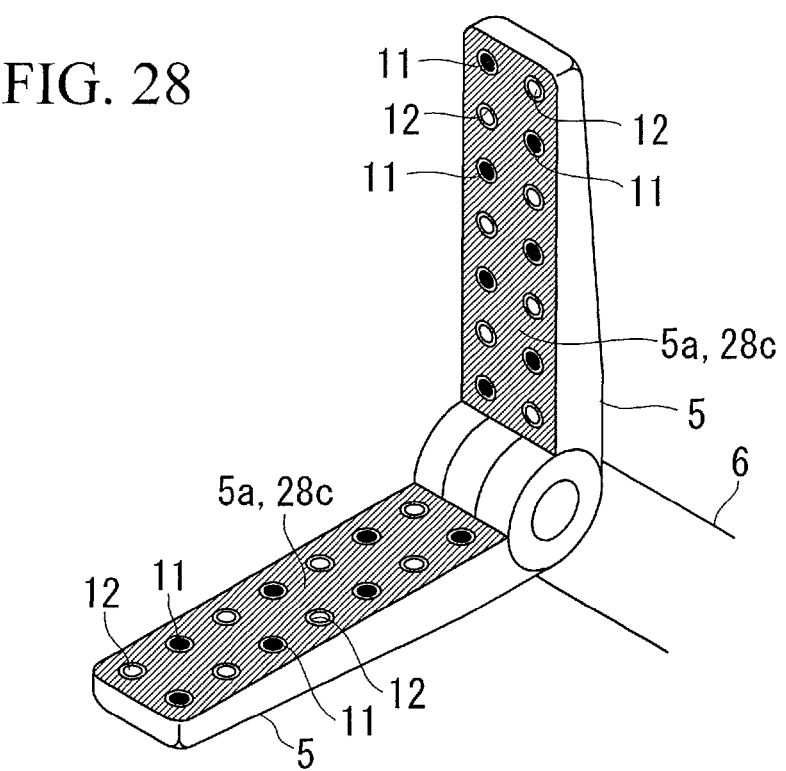
FIG. 28 is a partial perspective view illustrating a modification of the electrodes of the biological-tissue joining apparatus in FIG. 23.

When an adhesive that is cured by being irradiated with ultrasound is discharged, as shown in FIG. 28, ultrasonic transducers 28c may be provided on the opposing surfaces 5a.

Figure 29:
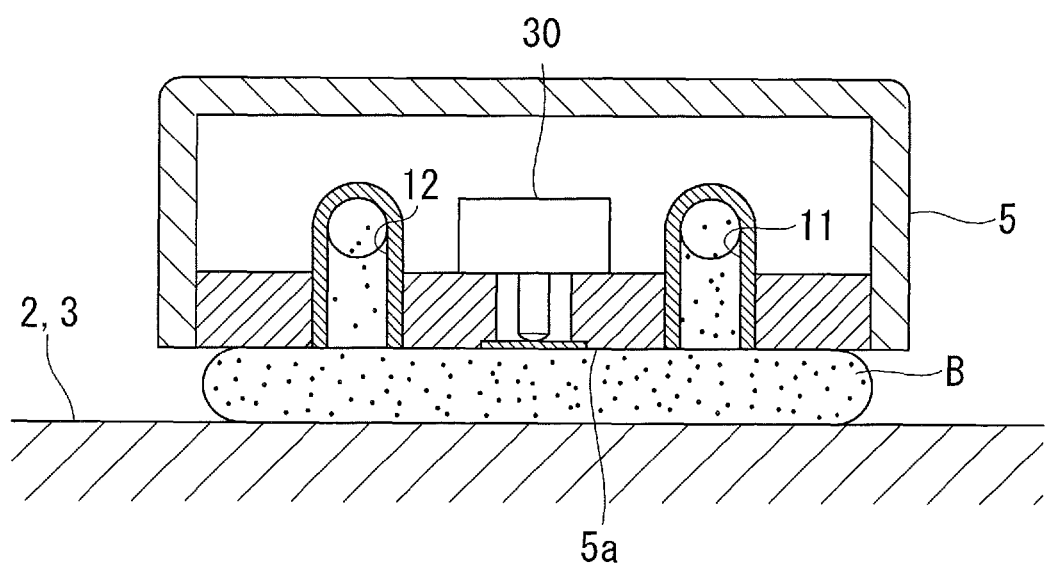
FIG. 29 is a lateral sectional view illustrating a modification of the electrodes of the biological-tissue joining apparatus in FIG. 23.
Figure 30:
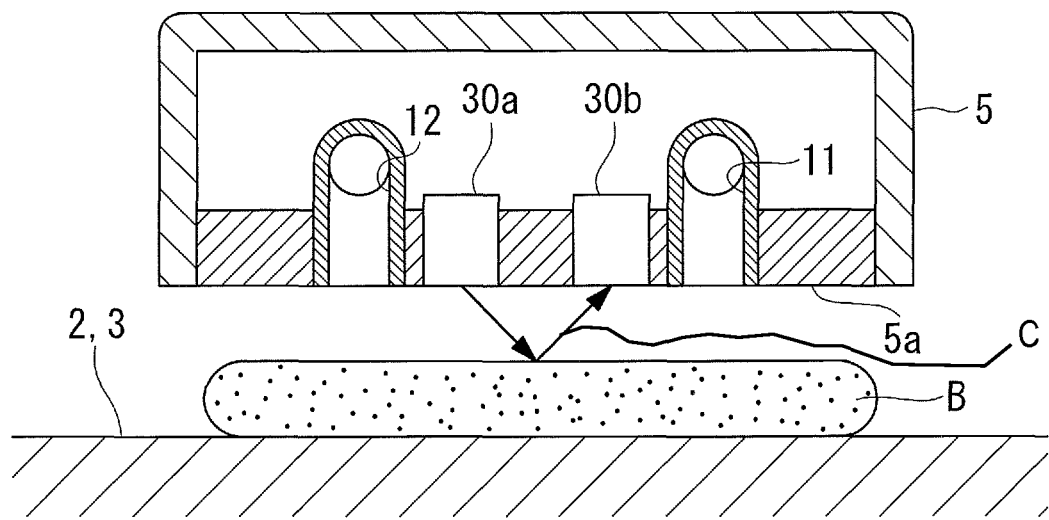
FIG. 30 is a lateral sectional view illustrating a state in which the hardness of an adhesive is measured by the electrodes of the biological-tissue joining apparatus in FIG. 29.

As shown in FIGS. 29 and 30, hardness sensors 30 that detect the hardness of the adhesive B discharged onto the intestinal tracts 2 and 3 may be disposed on the opposing surfaces 5a of the electrodes 5. As shown in FIG. 29, the hardness sensors 30 may be load sensors 30 that measure the load when the surface of the applied adhesive B is pushed. As shown in FIG. 30, the hardness sensors 30 may each include a light source 30a that irradiates the surface of the applied adhesive B with laser light C and a light-receiving part 30b that detects the laser light C reflected back from the surface of the adhesive B and may detect the hardness of the adhesive B according to a laser Doppler method.

Then, when it is determined whether or not to remove the electrodes by displaying the hardness information detected by the hardness sensors 30 on a display unit (alarm unit) (not shown) or when the energy supplying parts 28 and 29 that cure the adhesive B, as described above, are provided, the operation of the energy supplying parts 28 and 29 may be adjusted.

With this embodiment, the electrodes 5 exemplify a gripper that functions as an energy supplying unit for clamping, with pressure, the biological tissue to be joined, supplying energy to the biological tissue, and melting the collagen inside the biological tissue. Instead, however, the gripper may grip the biological tissue by clamping it without supplying energy. In such a case, a two-component adhesive may be discharged respectively from the discharge ports 11 and 12.

In this way, the adhesive is prevented from leaking from the gap between the biological tissue surface and the contact surfaces 5a by the leakage preventing parts, such as the peripheral-wall members 21, thus preventing the bonding of other tissue at sites other than the target site.

Therefore, it is possible to use not only fibrin-based adhesive composed of two types of blood-clotting components, fibrinogen and thrombin, but also adhesives having a greater adhesiveness, such as an aldehyde-based adhesive containing gelatin as an adhesive component and formaldehyde as a cross-linking component and an aldehyde-based adhesive containing albumin as an adhesive component and glutaraldehyde as a cross-linking component.

Figure 31:
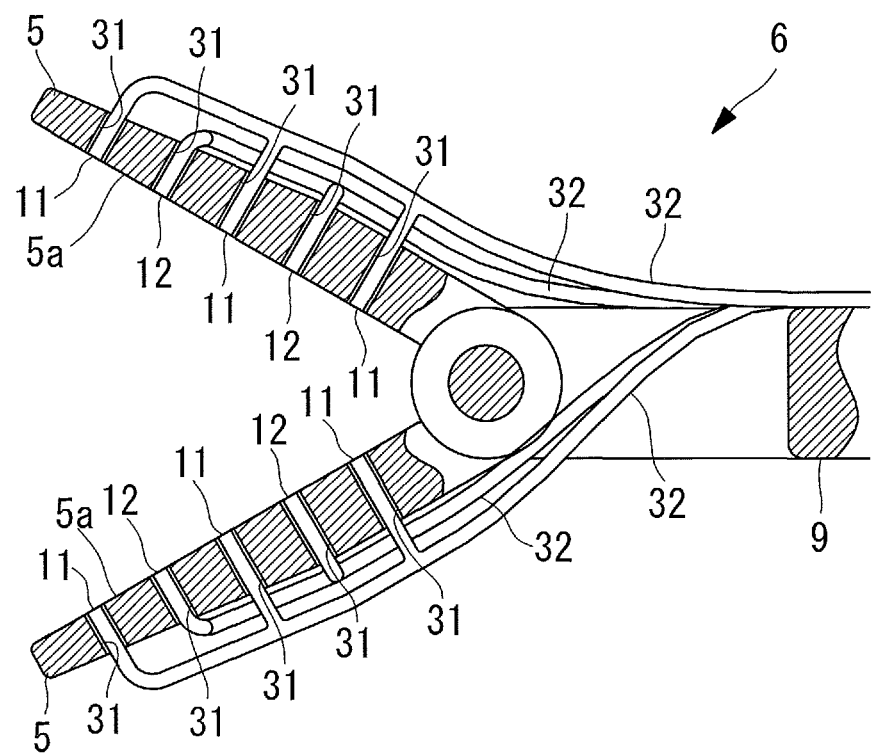
FIG. 31 is a partial longitudinal sectional view illustrating the structure of electrodes in a modification of the biological-tissue joining apparatus in FIG. 1.

With this embodiment, as shown in FIG. 31, through-holes 31 may be formed in the electrodes of the apparatus main body 6 at positions opposing the discharge ports 11 and 12, and an adhesive may be discharged from the discharge ports 11 and 12 at the tips of tubes 32 inserted in the through-holes 31 in a removable manner. An adhesive supplying part that discharges an adhesive from the opposing surfaces 5a of the electrodes 5 is formed of the through-holes 31 and the tubes 32. With this formation, there is an advantage in that even when clogging of a tube 32 by the cured adhesive occurs, by replacing the tube 32 with a new tube 32, the clogging can be removed, and the adhesive can be stably discharged.

Figure 32:
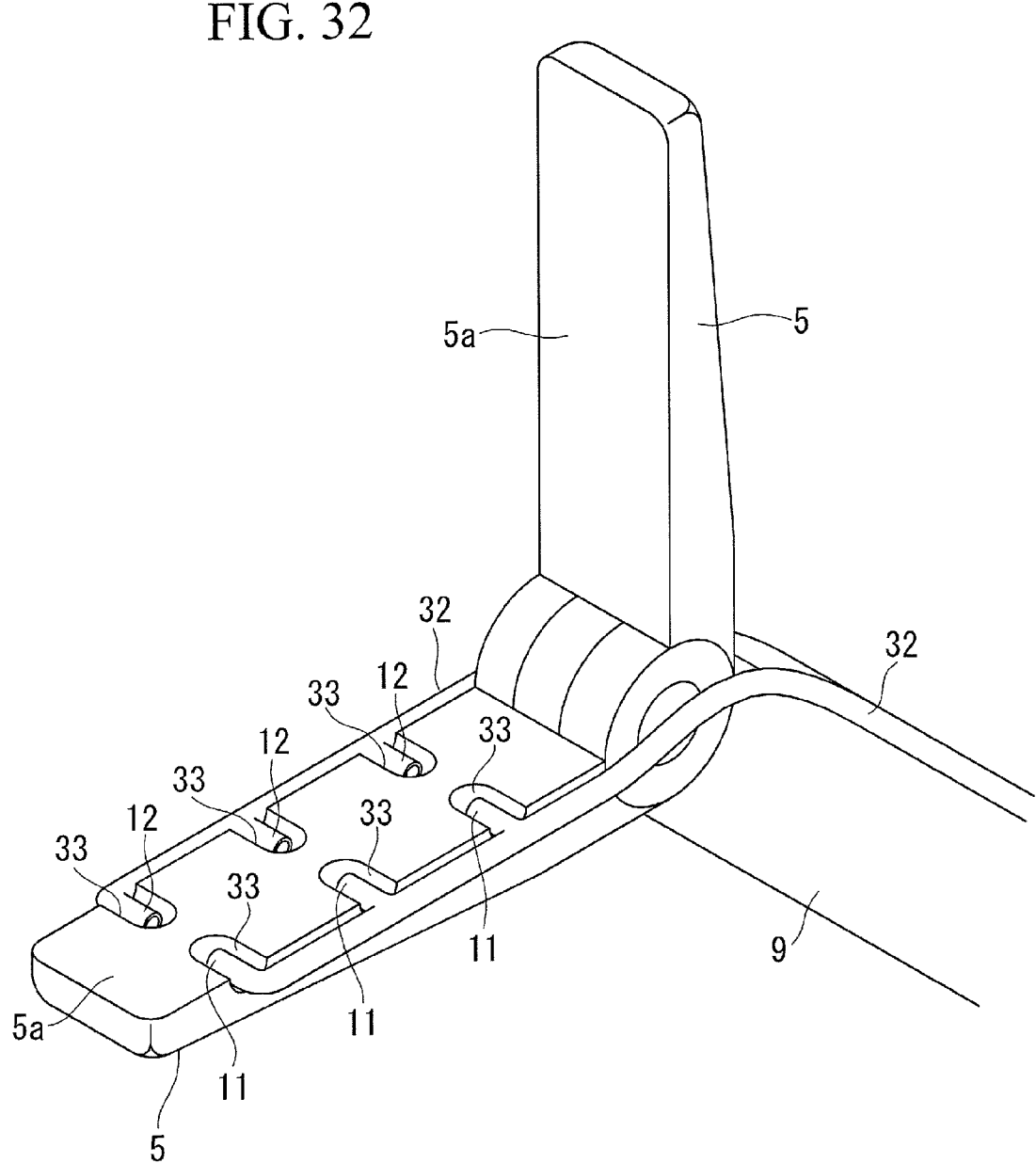
FIG. 32 is a partial perspective view illustrating the structure of electrodes in another modification of the biological-tissue joining apparatus in FIG. 1.

The method of attaching and removing the tubes 32 to and from the electrodes 5 may be any method, such as that shown in FIG. 31 in which the tubes 32 may be inserted into the through-holes 31 formed in the electrodes 5 or that shown in FIG. 32 in which the tubes 32 are extended along the external surfaces of the rod 9 and the electrodes 5 and required points are secured with securing members (not shown). The example shown in FIG. 32 is configured such that notches 33 are formed in one of the electrodes to accommodate the tips of the tubes 32, and the adhesive discharged from the discharge ports 11 and 12 flows out of the notches 33 toward the opposing surfaces 5a.

Figure 33:
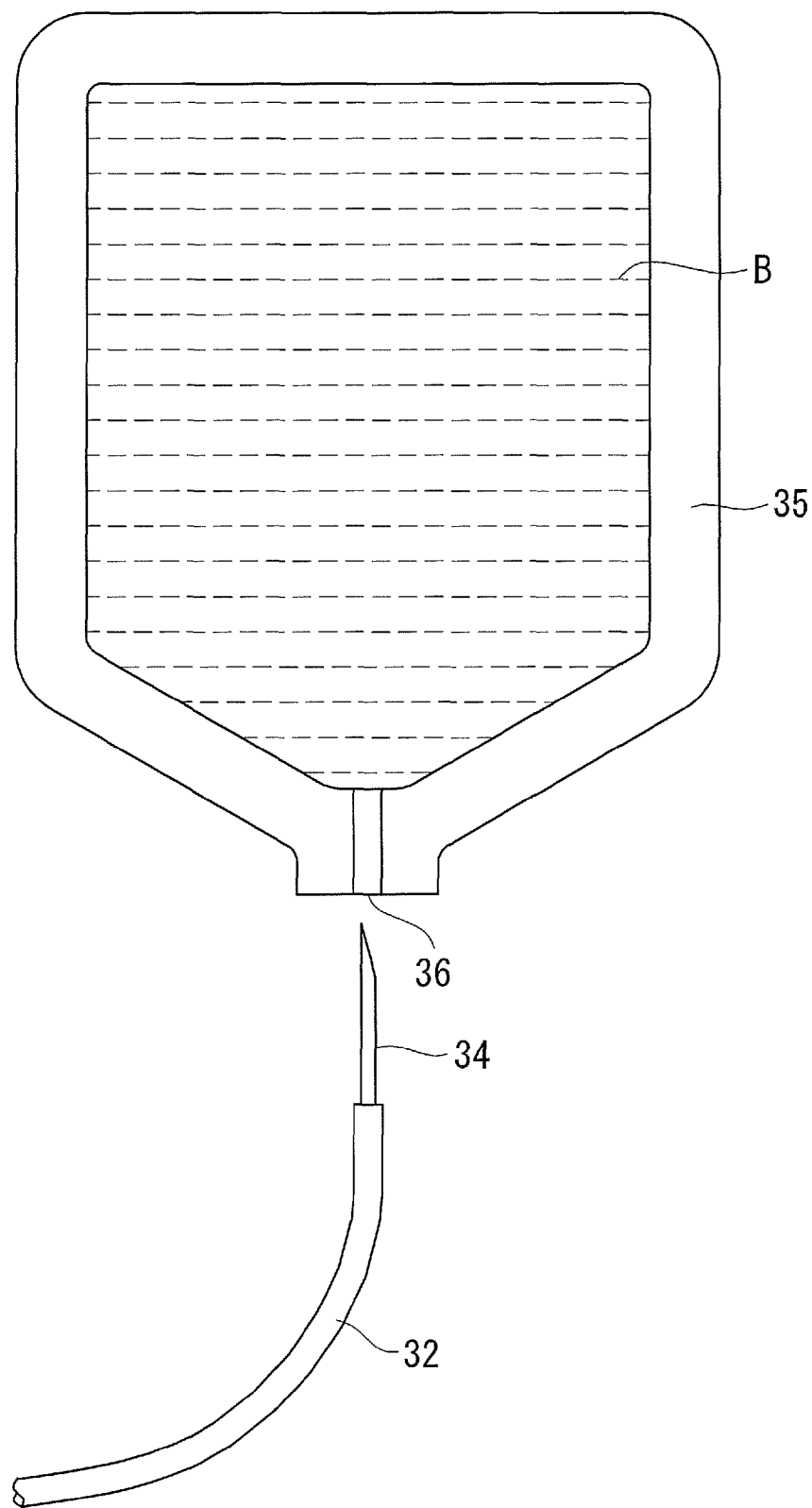
FIG. 33 is a partial front view for describing the connection structure of a tube and an adhesive container in another modification of the biological-tissue joining apparatus in FIG. 1.

The tubes 32 may be attached to or removed from supply ports of the tanks 13 accommodating the adhesive. Instead, however, the adhesive B inside adhesive containers 35 may be supplied to the discharge ports 11 and 12 via the tubes 32, as shown in FIG. 33, by providing needle members 34 at the other ends of the tubes 32 and then puncturing puncture parts 36 of the adhesive containers 35 that are sealed with the adhesive B contained inside, in a manner similar to a blood transfusion pack.

Figure 34:
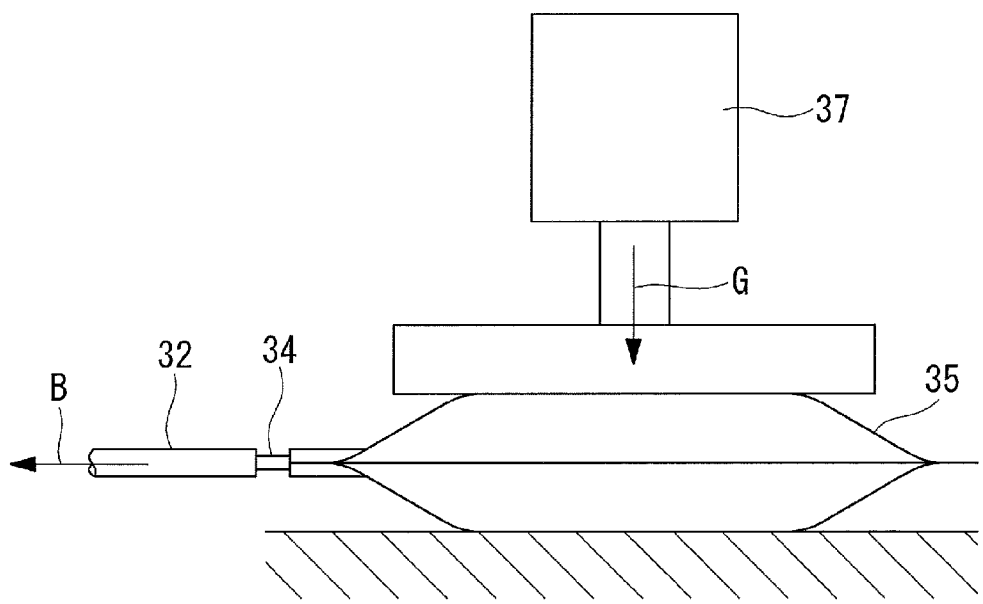
FIG. 34 is a diagram for explaining a compressing device that discharges an adhesive from the adhesive container in FIG. 33.

In such a case, as shown in FIG. 34, instead of the syringe-shaped tanks 13, it is preferable that compressing devices 37, such as air cylinders compressing the adhesive containers 35, be provided. By adjusting the pressure G of compressing the adhesive containers 35 with the compressing devices 37, the discharge rates of the adhesive B through the tubes 32 can be adjusted.

When the tubes 32 and the adhesive containers 35 that can be punctured with the needle members 34 provided on the tubes 32 are used, the tubes 32 may be formed of flexible elastic material and peristaltic pumps 38 that crush the tubes 32 in the radial direction at intermediate positions in the longitudinal direction and pump out the adhesive B therein may be used.

Figure 35:
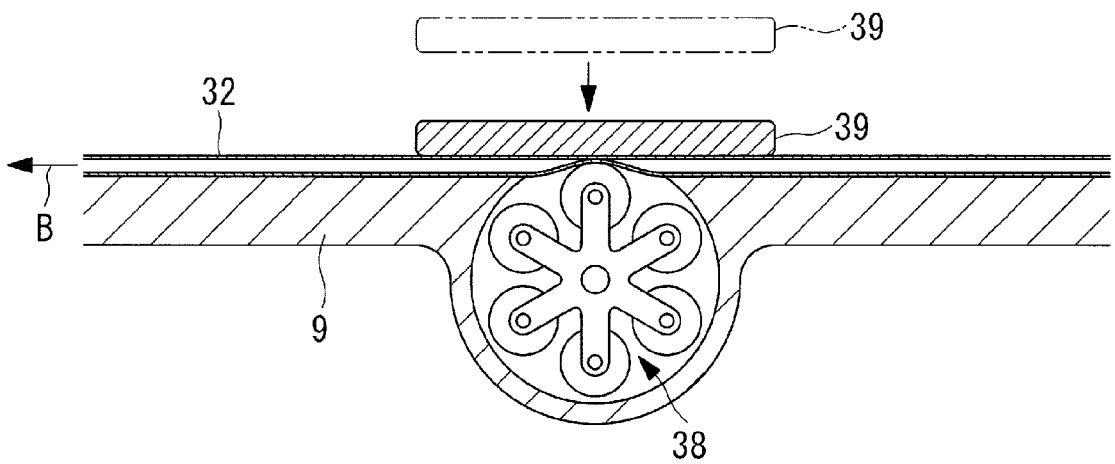
FIG. 35 is a longitudinal sectional view illustrating a peristaltic pump that pumps out an adhesive in a tube in another modification of the biological-tissue joining apparatus in FIG. 1.

In such a case, as shown in FIG. 35, it is preferable that the peristaltic pumps 38 be secured in intermediate positions along the rod 9 and pushing members 39 that can be opened and closed are provided such that the tubes 32 are clamped between the pushing members 39 and the peristaltic pumps 38.

As shown in FIG. 35 with the broken line, by disposing the tubes 32 in such a manner to cross over the peristaltic pumps 38 with the pushing members 39 opened and then closing the pushing members 39 as shown with the solid line in FIG. 35, the tubes 32 can be compressed in the radial direction. In this state, by driving the peristaltic pumps 38, the adhesive B inside the tubes 32 can be pumped out.

Figure 36:
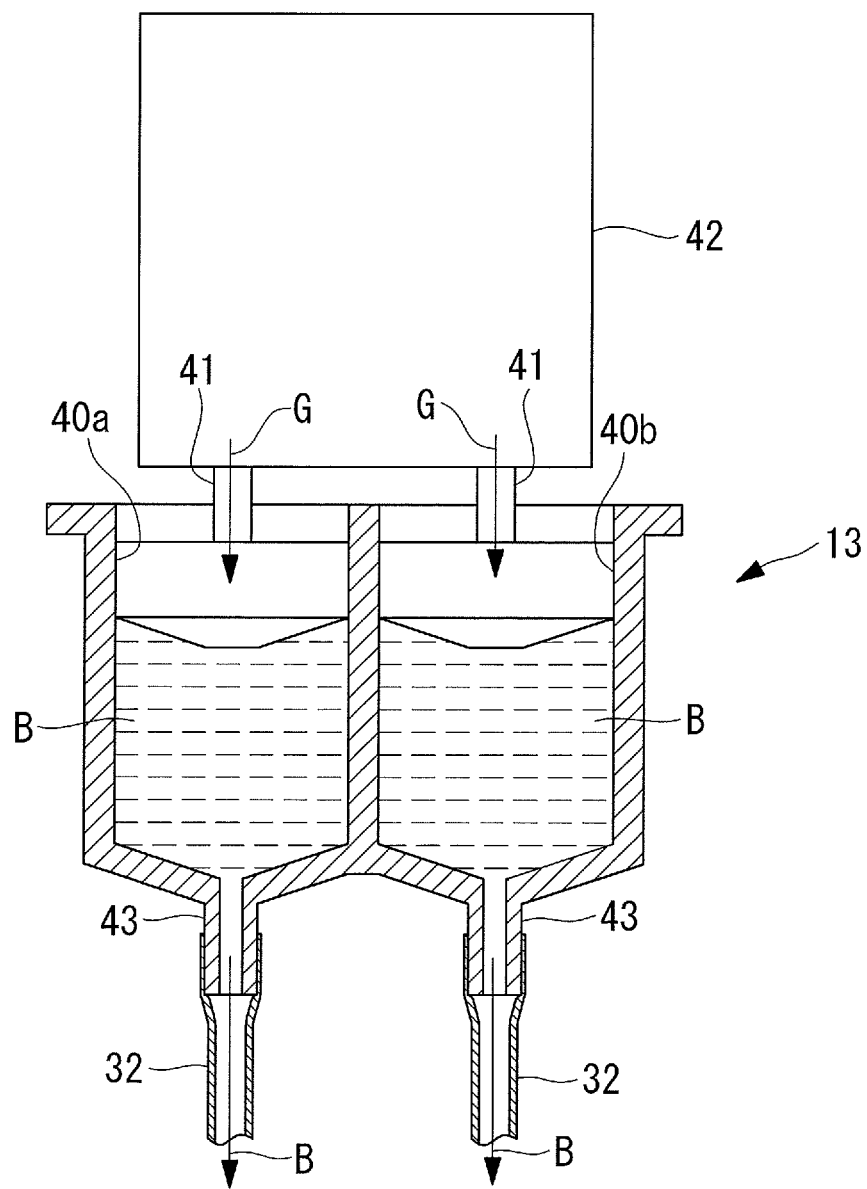
FIG. 36 is a longitudinal sectional view for describing a syringe for discharging an adhesive in another modification of the biological-tissue joining apparatus in FIG. 1.

When the cylinder-shaped tanks 13 are used, as shown in FIG. 36, accommodation parts 40a and 40b that separately accommodate the adhesive B (two types of adhesives are used in the example shown in the drawing), pistons 41 that push out the adhesive B inside the accommodation parts 40a and 40b, and pressure devices 42, such as air cylinders, that applies pressure G to the pistons 41 may be provided. By connecting the tubes 32 to supply ports 43 connected to the accommodation parts 40a and 40b and operating the pressure device 42, the adhesive B can be discharged from the discharge ports 11 and 12 of the electrodes 5, and the discharge rate can be adjusted by adjusting the pressure G of the pressure device 42.

In this case, it is preferable that the accommodation parts 40a and 40b be formed of transparent material and that scales (not shown) be provided on their outer surfaces. In this way, the supplied amount of the adhesive B can be visually observed from outside.

Figure 37A:
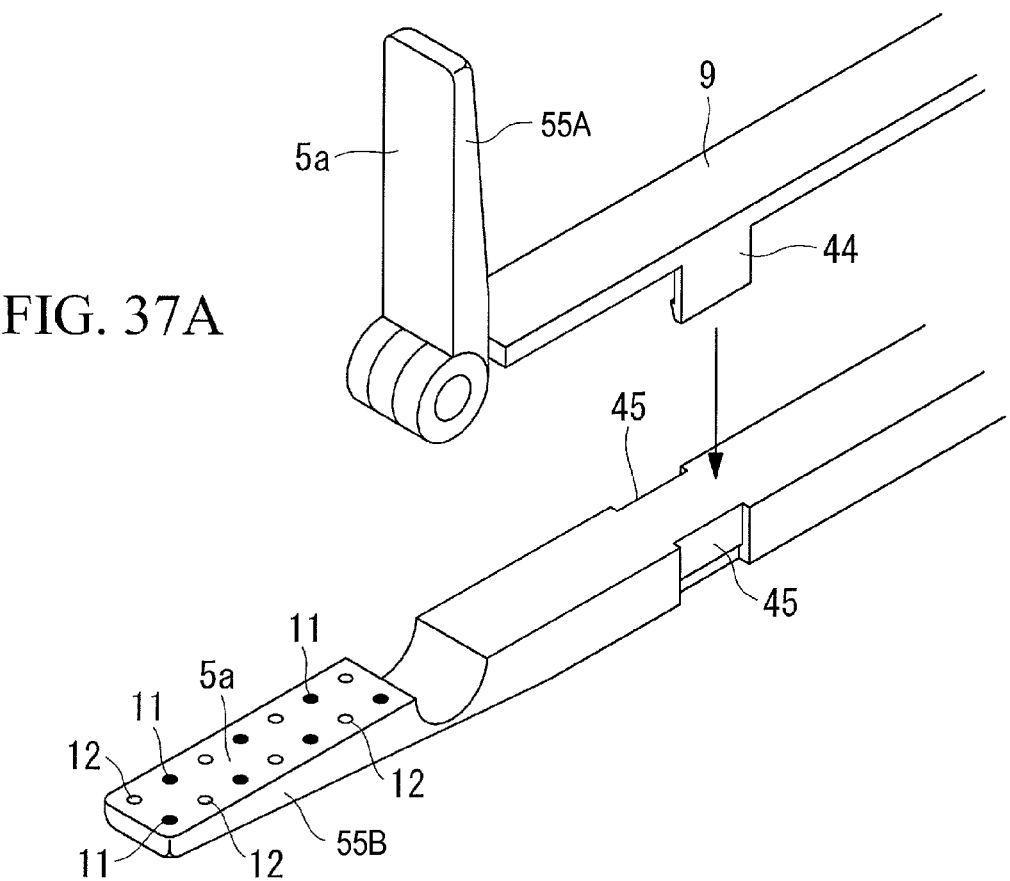
FIG. 37A is a partial exploded perspective view for describing a structural example of another modification of the biological-tissue joining apparatus in FIG. 1, in which one of the electrode members is a disposable component.
Figure 37B:
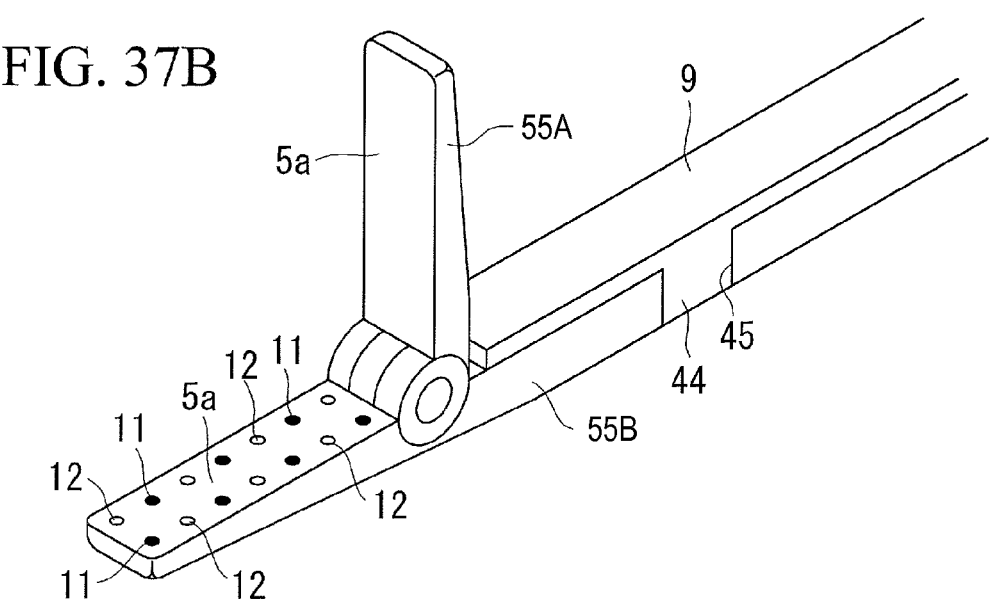
FIG. 37B is a partial assembled perspective view for describing a structural example of another modification of the biological-tissue joining apparatus in FIG. 1, in which one of the electrode members is a disposable component.

As shown in FIGS. 37A and 37B, a first electrode member 55A provided on the rod 9 in such a manner that it rotates and connected to a power source and a second electrode member 55B provided with a supply channel (not shown) for the adhesive B and the discharge ports 11 and 12 may be configured in a removable manner, and the second electrode member 55B may be replaced as a disposable component.

In FIGS. 37A and 37B, reference numeral 44 represents engagement parts composed of resilient pieces that secure, in a removable manner, the second electrode member 55B to the rod 9. Reference numeral 45 represents grooves that accommodate the engagement parts 44.

What is claimed is:

1. A biological-tissue treating apparatus comprising:
a gripper that clamps biological tissue to be joined; and
an adhesive supplying part that supplies an adhesive to the biological tissue gripped by the gripper,
wherein the adhesive supplying part includes a discharge port that discharges the adhesive to a contact surface of the gripper in contact with the biological tissue and a leakage preventing part that prevents leakage of the adhesive having an adhesion force from a gap between the surface of the biological tissue and the contact surface when the adhesive is discharged from the discharge port, wherein the leakage preventing part includes a peripheral-wall member surrounding the periphery of the contact surface and blocks the adhesive that leaks from the gap between the contact surface and the surface of the biological tissue and wherein the peripheral-wall member is provided in such a manner that the peripheral-wall member protrudes toward the contact surface and includes a driving part that causes the peripheral-wall member to protrude.

2. The biological-tissue treating apparatus according to claim 1, wherein the gripper is an energy supplying part that clamps, with pressure, the biological tissue to be joined and supplies energy to the clamped biological tissue to melt collagen inside the biological tissue.

3. The biological-tissue treating apparatus according to claim 1, wherein the driving part is a spring member that biases the peripheral-wall member in a direction protruding from the contact surface.

4. The biological-tissue treating apparatus according to claim 1, wherein the leakage preventing part includes a suction port, disposed on an outer circumferential position on the contact surface, that sucks the adhesive discharged from the discharge port and a negative-pressure supplying part that evacuates the suction port to negative pressure.

5. The biological-tissue treating apparatus according to claim 4, wherein the suction port is disposed on a side surface adjacent to the contact surface of the energy supplying part.

6. The biological-tissue treating apparatus according to claim 1, wherein the leakage preventing part includes a washing-solution discharge port, provided in the proximity of the contact surface, that discharges a washing solution and a washing-solution supplying part that supplies the washing solution to the washing-solution discharge port.

7. The biological-tissue treating apparatus according to claim 6, wherein the leakage preventing part includes a washing-solution suction port disposed on an outer circumferential position on the contact surface and that sucks the washing solution that is discharged from the washing-solution discharge port and flows along the surface of the adhesive, and a negative-pressure supplying part that evacuates the washing-solution suction port to negative pressure.

8. The biological-tissue treating apparatus according to claim 1, wherein,
   the adhesive is an adhesive curable by a physical stimulus, and
   the leakage preventing part includes a stimulating part that applies the physical stimulus to the adhesive discharged onto the biological tissue.

9. The biological-tissue treating apparatus according to claim 1, wherein the leakage preventing part includes a hardness detector that detects the hardness of the adhesive applied to the biological tissue and an alarm unit that issues an alarm that the hardness detected by the hardness detector is smaller than a predetermined threshold.

* * * * *